United States Patent [19]
Oshima et al.

[11] Patent Number: 5,827,507
[45] Date of Patent: Oct. 27, 1998

[54] ULTRAVIOLET SHIELDING COMPOSITE FINE PARTICLES, METHOD FOR PRODUCING THE SAME, AND COSMETICS

[75] Inventors: Kentaro Oshima; Toru Nishimura; Yoshinobu Imaizumi; Shunji Kozaki; Keiichi Tsuto, all of Wakayama; Satoshi Sugawara; Kazuhiro Yamaki, both of Chiba; Makoto Torizuka, Kanagawa, all of Japan

[73] Assignee: Kao Corporation, Tokyo, Japan

[21] Appl. No.: 619,607

[22] PCT Filed: Sep. 28, 1994

[86] PCT No.: PCT/JP94/01609

§ 371 Date: Apr. 1, 1996

§ 102(e) Date: Apr. 1, 1996

[87] PCT Pub. No.: WO95/09895

PCT Pub. Date: Apr. 13, 1995

[30]     Foreign Application Priority Data

Oct. 1, 1993  [JP]  Japan ................................... 5-297200
Apr. 28, 1994 [JP]  Japan ................................... 6-114239

[51] Int. Cl.[6] .............................. A61K 7/42; A61K 7/00; C01B 7/19; C01B 13/14
[52] U.S. Cl. ........................... 424/59; 423/462; 423/592; 424/60; 424/400; 424/401
[58] Field of Search ................................ 424/59, 60, 400, 424/401; 423/462, 592

[56]              References Cited
                    PUBLICATIONS

Derwent WPI English Abstract of JP–A–1–143821, Jun. 6, 1989.
Derwent WPI English Abstract of JP–A–5–132662, May 28, 1993.
Derwent WPI English Abstract of JP–A–3–17011, Jan. 25, 1991.
Derwent WPI English Abstract of JP–B–59–15885, Apr. 12, 1984.
Derwent WPI English Abstract of JP–A–63–126818, May 30, 1988.
Derwent WPI English Abstract of JP–A–4–56312, Mar. 2, 1992.

*Primary Examiner*—Shelley A. Dodson
*Attorney, Agent, or Firm*—Birch, Stewart, Kolasch & Birch, LLP

[57]                ABSTRACT

The present invention is directed to ultraviolet shielding composite fine particles having transparency in a visible light region, comprising (a) matrix particles comprising an aggregate of primary particles having an average particles diameter of from 0.001 to 0.3 $\mu$m, said aggregate being formed while retaining the shapes of the primary particles; and (b) daughter particles having an average particle diameter of from 0.001 to 0.1 $\mu$m, said daughter particles being dispersed in and supported by said matrix particles, wherein said daughter particles have a smaller band gap energy than that of particles constituting said matrix particles, and possess capability of absorbing ultraviolet light. The composite fine particles are produced by preparing a liquid mixture containing a mixture comprising starting materials for matrix particles and for daughter particles; forming droplets from the liquid mixture; and drying the formed droplets and/or pyrolyzing starting materials for pyrolysis therein. The cosmetics of the present invention contain the above composite fine particles.

22 Claims, 5 Drawing Sheets

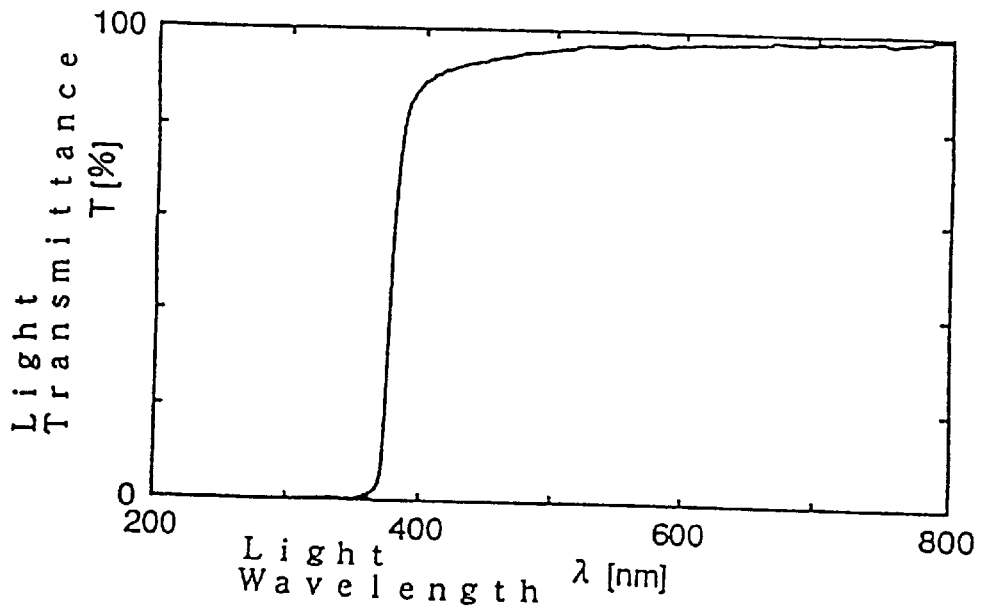
F I G. 4
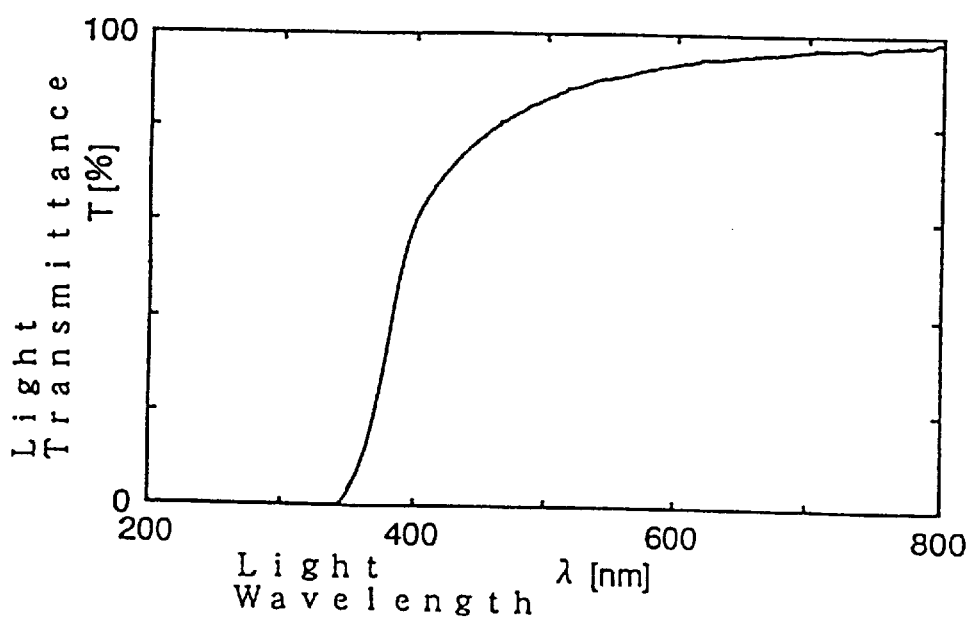
F I G. 5

ULTRAVIOLET SHIELDING COMPOSITE FINE PARTICLES, METHOD FOR PRODUCING THE SAME, AND COSMETICS

TECHNICAL FIELD

The present invention relates to ultraviolet shielding composite fine particles having high transparency in the visible light region and a high shielding ability in the ultraviolet region. It also relates to a method for producing the composite fine particles, and cosmetics containing such composite fine particles.

BACKGROUND ART

The sunlight reaching the earth includes infrared light, visible light, and ultraviolet light, of which 5 to 6% is ultraviolet light. The ultraviolet light has short wavelengths, and thus are electromagnetic waves with high energies. Therefore, ultraviolet light is known to decompose many kinds of materials and to cause various damages to a living body.

Therefore, ultraviolet shielding agents are used for the purpose of protecting skin from inflammation or skin cancer due to exposure of skins to harmful ultraviolet light by adding the ultraviolet shielding agents to the cosmetics. Also, they are used for the purpose of preventing a pigment from fading due to decomposition by ultraviolet light by mixing the ultraviolet shielding agents with paints. In these cases, by increasing transparency of such cosmetics or paints in the visible light region, unnatural skin whitening can be prevented, and change of coloring of paints can be prevented. Therefore, ultraviolet blocking is desirably carried out while maintaining transparency in the visible region.

The ultraviolet shielding agent using organic compounds as an effective component prevents transmission of the ultraviolet light by characteristic absorption of ultraviolet light by the component. For example, an ultraviolet absorbent composition comprising substituted N,N'-bis-aromatic formamidines is known (Japanese Patent Examined Publication No. 61-09993). However, the organic ultraviolet shielding agents have a problem that although they can absorb the ultraviolet light, at the same time they are likely to be decomposed by the light, and thereby the shielding ability undesirably lowers with the passage of time. As for their applications to cosmetics, the kinds and amounts of the ultraviolet shielding agents are restricted owing to effects caused on human bodies, making it difficult to achieve a good shielding performance within the regulated range.

On the other hand, the ultraviolet shielding agent using an inorganic compound contains inorganic fine particles in its composition and prevents transmission of the ultraviolet light by the absorbing ability and the scattering ability of the composition to the ultraviolet light. The inorganic ultraviolet shielding agent is superior to the organic ultraviolet shielding agent from the viewpoint that the composition containing the inorganic ultraviolet shielding agent is not decomposed by the ultraviolet light with the passage of time and has little effects to the human body.

However, since the inorganic ultraviolet shielding agents are in the form of particles, blocking of the ultraviolet light while maintaining high transparency in the visible light region by using the inorganic ultraviolet shielding agent has been known to be difficult when compared with the organic ultraviolet shielding agent.

In order to effectively exhibit light shielding ability in the ultraviolet region while maintaining high transparency in the visible light region, the composition has to be microgranulated to give ultrafine particles capable of being in a highly dispersed state to increase ultraviolet scattering ability. However, in the case of using ultrafine particles, problems may occur in dispersion stability due to aggregation of the ultrafine particles.

In order to improve dispersability, a surface of the ultrafine particles may be coated with other materials. For example, skin cosmetics comprising an oily cosmetic base material and a hydrophobic titanium oxide powder are known (Japanese Patent Examined Publication No. 59-15885). However, a solvent has to be suitably selected depending upon the properties of the coating materials coated on the surface. Also, even if the surface treatment is conducted, since the particles are still ultrafine, the extent of lowering aggregation of the ultrafine particles is limited.

In order not to lower the ultraviolet scattering ability by the aggregation of the inorganic ultrafine particles, composites of the inorganic ultrafine particles are often formed with other relatively large carrier particles. For example, a thin flaky material dispersed with metal compound fine particles is known (Japanese Patent Laid-Open No. 63-126818). However, this publication does not refer to the fine particles for improving both the shielding ability in the ultraviolet region and the transparency in the visible light region. Also, the thin flaky particles have larger frictional resistance among the particles when compared with the spherical particles. Therefore, when the thin flaky particles are used for cosmetic base materials, skin texture does not seem to be good.

Japanese Patent Laid-Open No. 6-116119 discloses cosmetics having high ultraviolet absorption containing a flaky glass of a titania-silica glass comprising 5 to 80% by weight of titania and 20 to 95% by weight of silica, the total amount of titania and silica being at least 80% by weight. However, facilities necessitated to produce a glass is large, making it industrially disadvantageous.

Further, composite fine particles comprising ultrafine particles dispersed in and supported by the solid material are proposed. Conventional ultraviolet shielding composite fine particles include, for example, a composite powder in which a fine particle powder such as $TiO_2$ is uniformly dispersed in plate particles of metal oxides such as $SiO_2$ (Japanese Patent Laid-Open No. 1-143821); and composite particles in which a zirconium oxide powder or an aluminum oxide powder is carried on a surface of the matrix particles comprising such materials as nylon resins, silicone resins, and silicon oxide, and a titanium oxide powder or a zinc oxide powder is dispersed in an inner portion of the matrix particles (Japanese Patent Laid-Open No. 2-49717).

In order to use the above composite particles as ultraviolet shielding agents, the composite particles have to be usually dispersed in a medium in the actual serviceable environment. In this case, a recent research conducted by the present inventors has revealed that when the difference between the refractive index of the composite particles and that of the medium is large, light scattering takes place at an interface of the composite particles and the medium, thereby making both the transparency in the visible light region and the shielding ability in the ultraviolet region poor. Although these problems are yet to be solved, they have not been considered in the above publications.

Further, Japanese Patent Laid-Open No. 4-65312 is concerned with metal compound-containing porous silica beads, the production method thereof, and the powder deodorant. In this publication, the metal compound fine particles having a primary particle diameter of 0.001 to 0.3 µm are contained in the porous silica beads in an amount of from 0.1 to 30% by weight, and the porous silica beads do not substantially contain any voids of not less than 0.3 µm. In this case, when the metal compound fine particles contained therein are suitably selected so as to have a refractive index close to the refractive index of silica (the refractive index being in the range of from 1.4 to 2.0), silica particles with further improved transparency can be obtained. However, the range for the refractive index of the metal compound fine particles contained in the inner portion of the composite particles is merely disclosed, none of the total refractive index of the composite particles being disclosed.

As explained above, in order to solve the problems inherent in the ultrafine ultraviolet shielding agents, several attempts have been made to use composites of mainly metal oxides. However, many of the compounds exhibiting good ultraviolet absorption, such as $TiO_2$ and ZnO, have relatively high refractive indices, so that the composite fine particles incorporating these ultrafine particles have refractive indices notably higher than an aqueous solution, conventional organic solvents, polymers, etc. When the above composite fine particles are dispersed in a medium, the present inventors have found that light scattering in the visible light region takes place at the interface of the composite fine particles and the medium, and thereby the transparency of the medium is drastically lowered. However, a technical idea of controlling the refractive index of the ultraviolet shielding particle of the composite fine particles has not been proposed so far.

In the fields of resin fillers, fluorine-based inorganic compounds, such as $MgF_2$ and $CaF_2$, or fluorine-based organic polymeric compounds, such as polyethylene tetrafluoride, which are known as low-refractive index materials having high transparency, are added to powders, etc. as starting materials to lower the refractive index.

For instance, Japanese Patent Laid-Open No. 4-85346 discloses a glass powder, used as a transparent inorganic powder for resin fillers, comprising metal oxides, such as $SiO_2$, $Al_2O_3$, $B_2O_3$, BaO, SrO, ZnO, and MgO, and metal fluorides, the glass powder having a refractive index ($n_D$) adjusted in the range of from 1.44 to 1.70. The publication describes that the glass powder has high light transmittance, and it does not show strong alkalinity, so that the resins do not substantially undergo deterioration. Also, they are significantly stabilized in resin hardening. However, the publication merely describes that a highly transparent inorganic powder for resin fillers can be obtained by changing the compositional ratio of the materials, and the above metal oxides, etc. are not present in the state of particles in the final product powder due to the high-temperature melting production, and this publication does not refer to ultraviolet shielding ability. Further, this publication does not refer to the compositional dependency of the refractive index of powders.

Japanese Patent Examined Publication No. 3-43201 discloses a method for producing a spherical fine particle powder containing composite inorganic oxides, comprising the step of spraying and drying a colloidal solution comprising not less than two kinds of inorganic oxides, each kind of the inorganic oxides being contained in an amount of not less than 5% by weight in a dry atmosphere at a temperature of from 10° to 100° C. to produce powders having an average particle diameter of 1 to 20 µm. The obtained composite fine particles can be used for various applications, such as high-grade lubricating fillers, body color for ink, and toners. Thus, the publication does not refer to a production of composite fine particles having both a good shielding ability in the ultraviolet range and high transparency in the visible light range.

DISCLOSURE OF THE INVENTION

An object of the present invention is to provide ultraviolet shielding composite fine particles having high transparency in the visible light region and high shielding ability in the ultraviolet region.

Another object of the present invention is to provide a method of producing such ultraviolet shielding composite fine particles.

A further object of the present invention is to provide cosmetics containing such ultraviolet shielding composite fine particles.

The present inventors have found composite fine particles comprising daughter particles having a good ultraviolet shielding ability (i.e., ultraviolet scattering ability and absorption ability) and matrix particles in which the daughter particles are dispersed and by which the daughter particles are supported. Also, the present inventors have found that the advantageous effects of the ultrafine particles can be achieved to its optimum by a suitable combination of the matrix particles and the daughter particles based on the difference in band gap energies therebetween.

Further, in the control of the refractive index of the composite fine particles, the present inventors have found that in the case where the refractive index of the composite fine particles is substantially equal to the refractive index of the medium, the refractive index being able to be controlled by a suitable combination of the matrix particles containing metal oxides and low-refractive index fluorine compounds and the daughter particles, light scattering is well-restricted at the interface of the composite fine particles and the medium. In this case, regardless of the shapes of the composite fine particles being spherical, plate-like, or acicular, or regardless of the surface roughness of the composite fine particles, the light can be well transmitted into the inner portion of the composite fine particles. Therefore, the transparency in the visible light region is remarkably improved, and a high shielding ability in the ultraviolet region is well exhibited by the function of the ultrafine particles dispersed in the inner portion of the composite fine particles. Also, the present inventors have found that when fine particles having a low-refractive index and a particle diameter of not more than 0.3 µm are used, the total refractive index of the composite fine particles can be lowered without causing scattering of the visible light even when a domain of a fine particle size is formed in the inner portion of the composite fine particles.

The present inventors have found that the ultraviolet shielding composite fine particles containing daughter particles evenly dispersed in and supported by the matrix particles can be continuously produced by atomizing and drying and/or pyrolysis of starting materials for the daughter particles and the matrix particles.

The gist of the present invention is as follows:

(1) Ultraviolet shielding composite fine particles having transparency in a visible light region, comprising:

(a) matrix particles comprising an aggregate of primary particles having an average particle diameter of from 0.001 to 0.3 µm, the aggregate being formed while retaining the shapes of the primary particles; and (b) daughter particles having an average particle diameter of from 0.001 to 0.1 µm, the daughter particles being dispersed in and supported by the matrix particles, wherein the daughter particles have a smaller band gap energy than that of particles constituting the matrix particles, and possess capability of absorbing ultraviolet light;

(2) A method for producing ultraviolet shielding composite fine particles having transparency in a visible light region comprising matrix particles and daughter particles dispersed in and supported by the matrix particles, comprising the steps of:

(a) preparing a liquid mixture containing less than 5% by weight of a mixture comprising starting materials for the matrix particles and starting materials for the daughter particles, prepared by mixing:

(i) starting materials for matrix particles selected from the group consisting of a sol containing particles constituting the matrix particles, primary particles of the matrix particles having an average particle diameter of from 0.001 to 0.3 $\mu$m, a solution capable of producing the particles constituting the matrix particles by a pyrolysis reaction, and mixtures thereof; and (ii) starting materials for daughter particles selected from the group consisting of a sol containing daughter particles having an average particle diameter of from 0.001 to 0.1 $\mu$m, a powder of the daughter particles, a solution capable of producing the daughter particles by a pyrolysis reaction, and mixtures thereof, so as to have a daughter particle concentration of from 0.1 to 50% by volume in a whole solid volume;

(b) forming droplets from the liquid mixture; and (c) drying the formed droplets and/or pyrolyzing starting materials for pyrolysis therein, the drying and/or pyrolyzing steps being carried out in an atmosphere of from 100° to 1000° C.; and (3) Cosmetics comprising ultraviolet shielding composite fine particles mentioned in (1) above.

When the composite fine particles of the present invention are dispersed in a solid or liquid medium, the composite fine particles show high light transmittance in the visible light region, and exhibit a high shielding ability in the ultraviolet region, the shielding ability being achieved by good scattering ability and absorbing ability of the daughter particles. Also, since daughter particles having a high catalyst activity are present in the inner portion of the matrix particles, the catalyst activity of the daughter particles gives very little effects to the medium around the composite fine particles. In other words, by forming composite fine particles with ultrafine particles having an ultraviolet shielding ability, the composite fine particles of the present invention can stably exhibit optical properties of the ultrafine particles having high transparency in the visible light region and having a high shielding ability in the ultraviolet region in a fine particle size for easy handling. Also, the composite fine particles of the present invention show no deterioration when formulated in cosmetics. The cosmetics of the present invention containing the composite fine particles have good smoothness, excellent extensibility on skin, substantially no unevenness, excellent transparency, no unnatural skin whitening, and high ultraviolet shielding effects. Further, since the composite fine particles of the present invention have excellent transparency, the coloring of the cosmetics is not affected, and hence, the amount of the composite fine particles added in the cosmetics can be widely varied.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 4 is a graph showing the relationship between a light wavelength and a light transmittance of the ultraviolet shielding composite fine particles obtained in Example 4, as measured by an ultraviolet-visible light spectrophotometer;

FIG. 5 is a graph showing the relationship between a light wavelength and a light transmittance of the ultraviolet shielding composite fine particles obtained in Example 5, as measured by an ultraviolet-visible light spectrophotometer;

Figure 1:
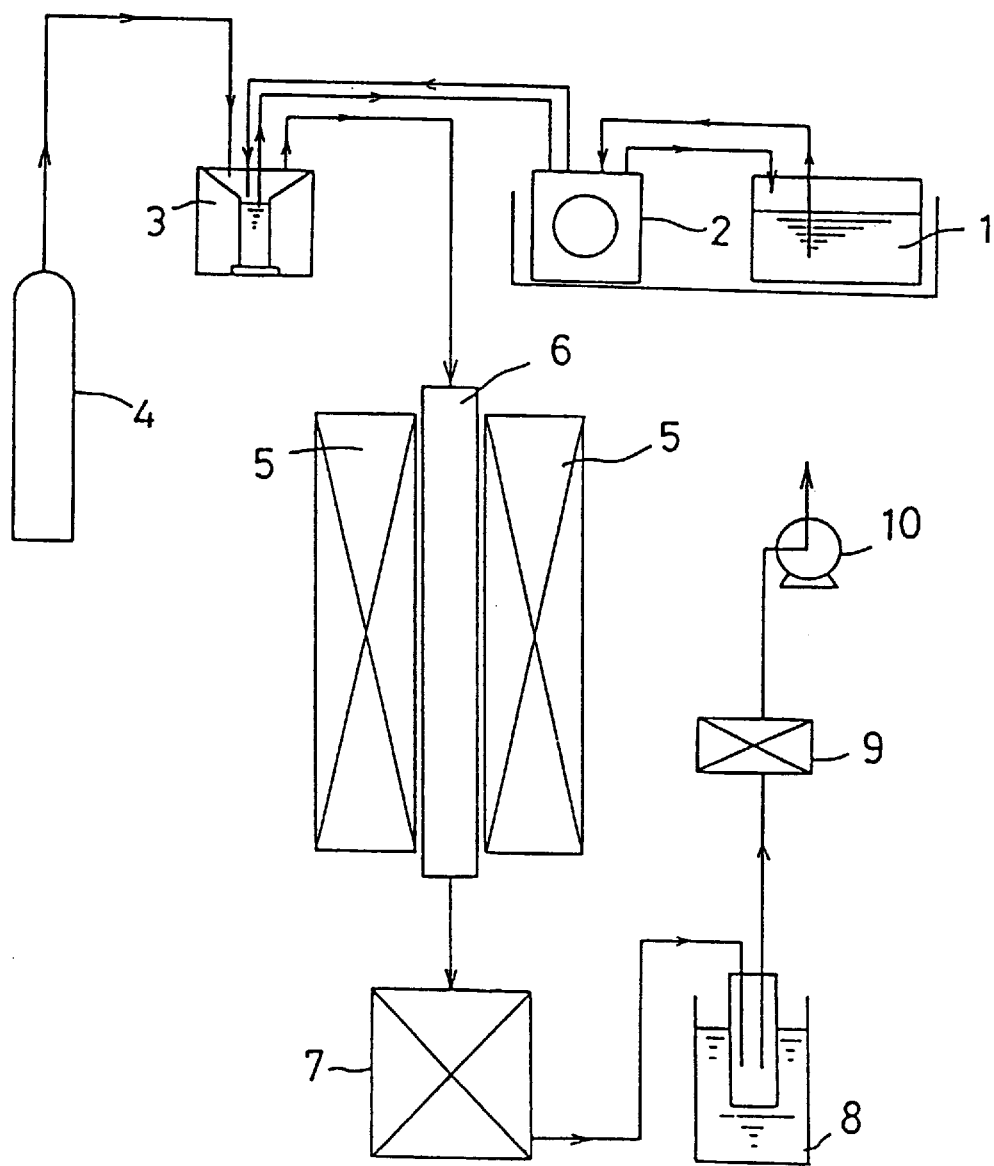
FIG. 1 is a schematic view showing an apparatus suitably used for producing ultraviolet shielding composite fine particles of the present invention.

The reference numerals in FIG. 1 denote the following elements:

Element 1 is a vessel, element 2 a pump for supplying fluids, element 3 an atomization device for starting material liquid mixture, element 4 a device for supplying a carrier gas, element 5 a heating member, element 6 a drying pipe or reaction pipe, element 7 an ultraviolet shielding composite fine particle collector, element 8 a cold trap, element 9 a filter, and element 10 a pump.

BEST MODE FOR CARRYING OUT THE INVENTION

Fine particles having a relatively small particle diameter and having a high shielding ability against the ultraviolet light are likely to form aggregates, so that the dispersion of the fine particles in a medium would be difficult so as to exhibit their function well. Therefore, by formation of a composite of the fine particles with relative large particles, namely by supporting the fine particles as daughter particles in matrix particles used as a carrier, the fine particles are maintained in a good dispersion state, thereby retaining their high shielding ability against the ultraviolet light. Also, since fine particles having generally a high surface activity are contained in the inner portion of the matrix particles, undesirably effects of the surface activity are inhibited from affecting a medium when the composite fine particles are suspended in the medium. In the present specification, the matrix particles of the composite fine particles refer to a matrix capable of containing and supporting daughter particles dispersed therein. The matrix particles are aggregates formed while retaining the shapes of the particles constituting the matrix particles (i.e., primary particles). The daughter particles refer to particles other than the matrix particles having an ultraviolet shielding ability.

Preferred embodiments of the present invention will be explained in detail below.

First, the properties of the composite fine particles, such as (1) a band gap energy of the particles, (2) a refractive index of the composite fine particles, and (3) grain boundaries of the particles, will be detailed below.

(1) Band gap energy of the particles

In the composite fine particles of the present invention, the fine particles used as the daughter particles have to have a good shielding ability against the ultraviolet light. The ultraviolet shielding ability is classified into two kinds: Absorbing ability of ultraviolet light and scattering ability of ultraviolet light.

The ultraviolet light absorption by inorganic compounds is ascribed to exciton absorption of mainly semiconductive compounds, and compounds having a band gap energy of from 3.0 to 4.0 eV effectively show such a property. Scattering of ultraviolet light is strongly exhibited as Mie scattering. In the case of high-refractive index materials, such as $TiO_2$, scattering is remarkably observed when the particle diameter of the material is about one-half the wavelength of the ultraviolet light, namely not more than 0.2 $\mu$m.

Since in ceramics a valence electron band and a conduction band are not continuous, it is known to absorb light having a wavelength corresponding to an energy not less than a band gap energy, the band gap energy referring to a difference between an energy level of the valence electron band and that of the conduction band. For instance, ZnO has a band gap energy of 3.2 eV, which absorbs a light having a wavelength of not more than 390 nm. The inorganic ultraviolet shielding agent absorbs ultraviolet light because its band gap energy corresponds to the wavelength of the ultraviolet light.

Therefore, in the composite fine particles of the present invention, in order for the daughter particles to effectively exhibit scattering ability and absorption ability of the ultraviolet light, the particles constituting the matrix particles have to have a band gap energy larger than that of the daughter particles. For instance, in the case of using aggregates of $TiO_2$ particles (rutile-type) as the matrix particles, and ZnO fine particles having a band gap energy smaller than that of $TiO_2$ as the daughter particles, the ultraviolet light having a wavelength of not more than 320 nm is absorbed by exciton absorption corresponding to a band gap energy of the particles constituting the matrix particles, namely $TiO_2$. Also, the ultraviolet light having a wavelength in the vicinity of 350 nm, which transmits through the matrix particles without being absorbed, is absorbed by exciton absorption corresponding to a band gap energy of the daughter particles while being multiply scattered by the daughter particles. Accordingly, the ZnO/$TiO_2$ (daughter/matrix) composite fine particles has a shielding ability against the ultraviolet light having a wavelength of not more than 350 nm. By contrast, when $TiO_2$ is used as the particles constituting the matrix particles and $SnO_2$ fine particles having a larger band gap energy than $TiO_2$ is used as the daughter particles, the ultraviolet light having a wavelength of not more than 320 nm is absorbed by exciton absorption corresponding to a band gap energy of the $TiO_2$ particles. However, the ultraviolet light having a wavelength in the vicinity of 320 nm, which transmits through the matrix particles without being absorbed, is not absorbed by exciton absorption corresponding to a band gap energy of $SnO_2$. Accordingly, the $SnO_2$/$TiO_2$ (daughter/matrix) composite fine particles cannot provide sufficient shielding effects against the ultraviolet light having wavelengths in the vicinity of 320 nm.

For the above reasons, in the composite fine particles of the present invention, the particles constituting the matrix particles have a band gap energy of preferably 3 to 9 eV, more preferably 5 to 9 eV. In order to more securely have the ultraviolet light reach the daughter particles by which absorption and scattering of the ultraviolet light can be achieved, a difference of the band gap energies between the daughter particles having a minimum band gap energy and the particles constituting the matrix particles is not less than 0.2 eV.

(2) Refractive index of composite fine particles

When the ultraviolet shielding composite fine particles are actually used, it is necessary to exhibit high transparency in the visible light region while maintaining a high shielding ability in the ultraviolet region. Here, in order to maintain a high shielding ability, a difference of the refractive indices between the matrix particles and the daughter particles has to be kept as large as possible because the ultraviolet shielding ability is remarkably improved when the difference of the refractive indices is kept large. In the present invention, the difference of the refractive indices is preferably not less than 0.1. For this reason, in the present invention, metal oxides and relatively low-refractive index fluorine compounds are used as materials constituting the matrix particles together with the daughter particles having relatively a high refractive index.

Also, in order to exhibit high transparency, a difference of the refractive indices between the composite fine particles and the medium has to be kept as small as possible. Thus, the refractive index of the composite fine particles has to be controlled in order to make the difference small. A feature of the present invention is to use fluorine compounds for controlling the refractive index.

In a suspension of the composite fine particles, namely in conditions to be used for cosmetics, etc., when the refractive index of the composite fine particles differs largely from that of the medium, transparency is likely to be lost because the visible light refracts or reflects at the interface of the composite fine particles and the medium. Here, the refractive index may be measured by a generally known immersion method (see Toshiharu Takou, et al., Optical Measurement Handbook, p. 475, 1981, published by Asakura Publishers). In this method, a refractive index of a medium, of which the highest light transmittance is obtained at a wavelength of 589.3 nm, is the refractive index of the sample. However, the operation for the immersion method is complicated, and time-consuming. The refractive index, for convenience, can be theoretically calculated from the refractive indices of the daughter particles and the primary particles of the matrix particles and the volume ratio therebetween. Since the theoretically calculated refractive index extremely approximates datum obtained by the immersion method depending on the composite fine particles, in such a case the refractive indices of the composite fine particles can be also obtained by a simple calculation method as mentioned above.

The refractive index $n_D^{20}$ of the generally used medium is 1.3 to 1.8. On the other hand, since many of metal oxides having a high shielding ability, such as $TiO_2$ and ZnO, have a refractive index $n_D^{20}$ of not less than 2.0, when the metal oxides are used as the daughter particles, the refractive index of the composite fine particles has to be approximated to that of the medium by using a low-refractive index material for the matrix particles. Specifically, the refractive index of the composite fine particles is 1.3 to 1.8, preferably 1.3 to 1.7, more preferably 1.4 to 1.5. Also, a difference of the refractive indices between the matrix particles and the daughter particles in the composite fine particles of the present invention is preferably not less than 0.1. By keeping the difference in the refractive indices, the scattering ability of the ultraviolet light is improved.

(3) Grain boundaries of particles

In the primary particles of the matrix particles, as the particle diameter becomes smaller, namely as the grain boundaries in the inner portion of the matrix particles become smaller, the visible light cannot detect the presence of the grain boundaries, so that the matrix particles are provided with transparency regardless of whether the primary particles of the matrix particles are crystallized. Since the daughter particles similarly comprise ultrafine particles, they also have good transparency. Therefore, the composite fine particles totally have good transparency.

Next, a method for producing ultraviolet shielding composite fine particles will be explained in detail by referring to the drawings.

FIG. 1 is a schematic view showing one example of an apparatus for producing ultraviolet shielding composite fine particles. Outlines of the method for producing the ultraviolet shielding composite fine particles will be explained referring to the figure.

Specifically, a starting material liquid for daughter particles having transparency in the visible light region and shielding ability in the ultraviolet region is uniformly blended in a vessel 1 with a starting material liquid for matrix particles. The obtained liquid mixture is continuously supplied to an atomization device 3 for generating fine starting material droplets using a pump 2 for supplying fluids, to give starting material droplets. The obtained starting material droplets are carried along with a carrier gas supplied from a device 4 for supplying a carrier gas into a drying pipe or reaction pipe 6 heated to a high temperature by means of a heating member 5 installed in the periphery thereof, so that a drying process of the droplets and/or a pyrolysis reaction of the starting materials are carried out therein to give ultraviolet shielding composite fine particles comprising the daughter particles and the matrix particles in a vapor-solid mixed state. The composite fine particles thus produced are collected using a fine particle collector 7. A gas discharged from a fine particle collector 7 passes through a cold trap 8 and a filter 9, while the obtained condensed liquid is removed. Thereafter, the remaining gas is forced to be discharged by a pump 10.

The shapes, sizes and materials for the vessel 1 are not particularly limited, and any ones can be used as long as the starting material liquid mixture comprising the starting material liquid for the daughter particles and the starting material liquid for the matrix particles can be stably stored.

The pump 2 for supplying fluids is preferably a pump having peristaltic movements, such as a peristaltic pump, with a particular preference given to a pump capable of supplying a given amount of the liquid mixture to the atomization device 3.

Examples of the atomization devices 3 of the starting material liquid mixture include atomization devices by ultrasonic vibration and binary-fluid-type nozzle atomizing devices. Among them, a preference is given to atomization devices by ultrasonic vibration from the view points of narrow distribution of droplet diameters and formation of only fine droplets.

As for the device 4 for supplying a carrier gas, any ones which can supply a given flow amount of the carrier gas for a long period may be used. As for a device for controlling a flow of the carrier gas, for instance, a mass flow meter, etc. may be used. Here, the carrier gas refers to an inert gas, or any gases which do not inhibit the progress of a drying process or a pyrolysis reaction, including, for instance, a helium gas, air, a nitrogen gas, an argon gas, etc.

The drying pipe or reaction pipe 6 is mainly used as a drying furnace and/or a furnace for pyrolysis, and examples of materials for the drying pipe or reaction pipe 6 include stainless steels, ceramics, silica glasses, etc. As for the heating member 5, any ones may be preferably used which can be temperature-controlled so as to take isothermal portions as large as possible in the drying pipe or reaction pipe in the shaft direction as well as in the radial direction of the pipe.

In the production of the composite fine particles, in the case of using sols containing the daughter particles or sols containing the particles constituting the matrix particles as the starting materials for the daughter particles or for the matrix particles as explained below, a drying process may be utilized. Alternatively, in the case of using starting materials capable of producing the daughter particles or particles constituting the matrix particles by pyrolysis (hereinafter abbreviated as "starting materials for pyrolysis"), a pyrolysis reaction is utilized.

Specifically, there are various kinds of embodiments for the starting material liquid given below, without intending to restrict the scope of the present invention thereto.

(1) Starting materials for daughter particles: sol
Starting materials for matrix particles: sol (2) Starting materials for daughter particles: sol and/or starting materials for pyrolysis
Starting materials for matrix particles: sol (3) Starting materials for daughter particles: sol
Starting materials for matrix particles: starting materials for pyrolysis (4) Starting materials for daughter particles: starting materials for pyrolysis
Starting materials for matrix particles: starting materials for pyrolysis (5) Starting materials for daughter particles: both sol and starting materials for pyrolysis
Starting materials for matrix particles: both sol and starting materials for pyrolysis When a drying process is employed, a hot-gas drying means may be employed instead of a drying means using a heated pipe.

In the embodiment (2) above, for example, hydroxides, such as $Ti(OH)_4$ and $Zn(OH)_2$, which are precursors of $TiO_2$ and ZnO, respectively, may be used as the starting materials for the daughter particles. Also, a sol containing $SiO_2$, etc. may be used as the starting materials for the matrix particles.

Examples of the pyrolysis reactions include the following:

| | |
|---|---|
| $Ti(SO_4)_2$ | $\rightarrow TiO_2 + SO_x$; |
| $CuSO_4$ | $\rightarrow CuO + SO_x$; |
| $Zn(NO_3)_2$ | $\rightarrow ZnO + NO_x$; |
| $MgCO_3$ | $\rightarrow MgO + CO_2$; |
| $Ce(NO_3)_3$ | $\rightarrow CeO_2 + NO_x$; |

-continued

| | |
|---|---|
| $SnCl_4 \cdot 5H_2O$ | $\rightarrow SnO_2 + 4HCl + 3H_2O$; and |
| $Na_2SiO_3 \cdot H_2O$ | $\rightarrow SiO_2 + 2NaOH$. |

As for the fine particle collector 7, a filter-type collector or electrostatic-type collector may be effectively used, with a preference given to an electric dust collector and a diffusion charge-type electrostatic collector for a long-term operation.

The materials, shapes, etc. of the cold trap 8 are not particularly limited, and a preference is given to those having a cooling function for condensing the solvent used for the preparation of the starting materials, the solvent being vaporized at this stage, and efficiently removing the solvent from the carrier gas. The materials, shapes, etc. of the filter 9 are not particularly limited, and a preference is given to a filter for aerosol and a bag-filter. The materials, shapes, etc. of the pump 10 are not particularly limited, and a preference is given to a blower for exhausting the carrier gas without substantially changing the flow of the gas in the apparatus for producing the fine particles.

Next, the method for producing ultraviolet shielding composite fine particles of the present invention will be explained.

The method of the present invention basically comprises the following three steps of:

(a) preparing a liquid mixture containing less than 5% by weight of a mixture comprising starting materials for the matrix particles and starting materials for the daughter particles, prepared by mixing:
  (i) starting materials for matrix particles selected from the group consisting of a sol containing particles constituting the matrix particles, primary particles of the matrix particles having an average particle diameter of from 0.001 to 0.3 μm, a solution capable of producing the particles constituting the matrix particles by a pyrolysis reaction, and mixtures thereof; and
  (ii) starting materials for daughter particles selected from the group consisting of a sol containing daughter particles having an average particle diameter of from 0.001 to 0.1 μm, a powder of the daughter particles, a solution capable of producing the daughter particles by a pyrolysis reaction, and mixtures thereof, so as to have a daughter particle concentration of from 0.1 to 50% by volume in a whole solid volume;

(b) forming droplets from the liquid mixture; and (c) drying the formed droplets and/or pyrolyzing starting materials for pyrolysis therein, the drying and/or pyrolyzing steps being carried out in an atmosphere of from 100° to 1000° C.

In preferred embodiments of carrying out the present invention, the steps (a) to (c) are exemplified as follows:

Step (a)
  (1) preparing a liquid mixture containing less than 5% by weight of a particle mixture prepared by mixing a sol containing particles constituting the matrix particles, primary particles of the matrix particles having an average particle diameter of from 0.001 to 0.3 μm and a sol containing daughter particles having an average particle diameter of from 0.001 to 0.1 μm, so as to have a daughter particle concentration of from 0.1 to 50% by volume in a whole solid volume; or
  (2) preparing a liquid mixture by disintegrating or pulverizing a powder of daughter particles having an average particle diameter of from 0.001 to 0.1 μm in a sol containing particles constituting the matrix particles, primary particles of the matrix particles having an average particle diameter of from 0.001 to 0.3 μm, so as to have a daughter particle concentration of from 0.1 to 50% by volume in a whole solid volume;

Step (b)
  forming droplets having an average droplet diameter of from 0.1 to 2000 μm from the liquid mixture; and Step (c)
  drying the formed droplets and/or pyrolyzing starting materials for pyrolysis therein, the drying and/or pyrolyzing steps being carried out in an atmosphere of from 100° to 1000° C.

Here, in the step (a) above for preparing the liquid mixture, when the powder of the daughter particles is used, the powder is preferably disintegrated or pulverized by subjecting to a treatment, such as a milling treatment or a high-pressure dispersion treatment to retain the dispersion state of the daughter particles in the liquid mixture.

Next, the starting materials used in the present invention will be explained in detail.

(1) Daughter particles

The daughter particles constituting the composite fine particles in the present invention maintain good transparency in the visible light region while having a good shielding ability in the ultraviolet region. Therefore, the daughter particles are required not to absorb the light in the visible light region and to have a particle diameter small enough not to scatter the visible light.

As for materials constituting the daughter particles, in order to satisfy the requirements that they do not absorb the visible light but absorb the ultraviolet light, a preference is given to materials having a wavelength for an exciton absorption of a band gap energy corresponding to the wavelengths in the ultraviolet region. Specifically, semiconductive compounds having a band gap energy of from 3.0 to 4.0 eV are preferred, including, for instance, $TiO_2$, $ZnO$, $CeO_2$, $SiC$, $SnO_2$, $WO_3$, $SrTiO_3$, $BaTiO_3$, and $CaTiO_3$, which characteristically exhibit the above property. Among them, $TiO_2$, $ZnO$, and $CeO_2$ are conventionally used as ultraviolet shielding agents, and these compounds may be used singly or in combination thereof as particularly preferred examples. In particular, in order to shield the ultraviolet light of both the ultraviolet region A (320 to 400 nm) and the ultraviolet region B (280 to 320 nm), $ZnO$ and $CeO_2$ are effectively used. Also, in order to shield the ultraviolet light of the ultraviolet region B, $TiO_2$ is effectively used. These materials can be used singly or in combinations thereof.

The shapes of the daughter particles are not particularly limited, and they may be spherical, plate-like or acicular. The particle diameter of the daughter particles is preferably substantially the same as that of the primary particles of the matrix particles from the viewpoint of giving good dispersion of the daughter particles in the matrix particles. Furthermore, as for the scattering ability of the light in the ultraviolet region, which is strongly exhibited by Mie scattering, scattering can be remarkably noted when the particle diameter is about one-half the wavelength of the ultraviolet light, namely, not more than 0.2 μm. Therefore, in order to satisfy both good transparency in the visible light region and good shielding ability in the ultraviolet region, the daughter particles have an average particle diameter of preferably not more than 0.2 μm, more preferably not more than 0.1 μm, particularly 0.001 to 0.1 μm, and more particularly not more than 0.05 μm. The "daughter particles" in the present invention refer to primary particles thereof singly dispersed in and supported by the matrix particles and/or aggregates of the primary particles. Therefore, the average particle diameter of the daughter particles may also mean the average particle diameter of the aggregates.

In the present invention, since in the inner portion of the composite fine particles the daughter particles are present preferably in a dispersed state, higher dispersability and stability of the daughter particles in a sol are desired. In order to achieve such states of the daughter particles in a sol, the surface of the daughter particles may be coated with other materials, or the daughter particles may be blended with a sol stabilizer. For instance, in the case where $TiO_2$ ultrafine particles are used as the daughter particles, the surface of the ultrafine particles may be coated with such compounds as $SiO_2$ and $Al_2O_3$ to improve dispersability. Alternatively, the ultrafine particles may be blended with a basic stabilizer, such as $NH_3$, to stabilize the state of the $TiO_2$ sol. Also, in the case where the fine particle powder is surface-treated to achieve good dispersion, the treated fine particles can be used as starting materials for the daughter particles. The sol used in the present invention refers to fluids containing particles which are generally unobservable by an ordinary electron microscope but having a particle diameter larger than that of an atom or that of a low molecular compound (see Iwanami Dictionary of Physics and Chemistry, Third Edition, published by Iwanami Publishers). Examples of sols include hydrosol of silica and suspension of $TiO_2$ ultrafine particles.

In the case of producing the daughter particles comprising metal compounds, solutions of the metal salts may also be used as the starting materials for the daughter particles (starting materials for pyrolysis). Examples of the metal salts include $Ti(SO_4)_2$, $TiCl_4$, $ZnSO_4$, $Zn(NO_3)_2$, and $Ce(NO_3)_3$. For example, in the case where ZnO is used as daughter particles, ZnO fine particles can be produced by atomizing and pyrolyzing an aqueous solution of $Zn(NO_3)_2$.

(2) Matrix particles

The matrix particles constituting the composite fine particles have to have good transparency in the visible light region in the same manner as the daughter particles in order to afford a good transparency to the composite fine particle suspension. Specifically, the matrix particles desirably are constituted by materials which do not absorb the visible light, and the primary particles of the matrix particles preferably do not have a particle diameter exceeding 0.3 $\mu$m. For instance, a preference is given to aggregates of the ultrafine particles, each of the ultrafine particles having an average particle diameter of 0.01 $\mu$m.

As for the materials constituting the matrix particles, materials having high transparency, such as ceramics, fluorine compounds, and mixtures thereof, may be used. For instance, metal oxides, fluorine compounds, and mixtures thereof may be used. As mentioned above, since the aggregates of the fine particles normally constitute the matrix particles, the fine particles (i.e. primary particles) constituting the aggregates have an average particle diameter of not more than 0.3 $\mu$m, specifically, from 0.001 to 0.3 $\mu$m, in order to satisfy the requirements for the matrix particles. A preference is given to those having an average particle diameter of not more than 0.2 $\mu$m, more preferably not more than 0.1 $\mu$m, particularly preferably not more than 0.05 $\mu$m. For the same reasons mentioned for the daughter particles, the surface of the particles constituting the matrix particles may be coated with other materials, or the fine particles may be blended with sol stabilizers. Here, the coating materials or the stabilizers used may be similar ones used for the daughter particles.

Many of the metal oxides are available in the form of chemically stable solids, so that the metal oxides can be suitably used for materials constituting the matrix particles. Examples of the metal oxides contained in the matrix particles include $TiO_2O$, $CuO$, $ZnO$, $MgO$, $CeO_2$, $SnO_2$, $SiO_2$, $Fe_2O_3$, $Al_2O_3$, $NiO_2$, and $MnO_2$. A preference is given to $SiO_2$ from the viewpoint of having a suitable refractive index and good transparency explained above. Also, a preference is given to fine particles of $SnO_2$, $In_2O_3$, $SiO_2$, and $ZnO$ from the viewpoint of using ceramic fine particles having a large band gap energy.

The matrix particles mentioned above can also be prepared by a pyrolysis reaction, wherein the starting materials for pyrolysis are pyrolyzed as described above. In this case, metal salts can be used as the starting materials. Examples of metal elements of the metal salts include alkali metals, alkaline earth metals, and transition metals. Specifically, examples of the alkali metals include Li, Na, K, Rb, Cs, and Fr. Examples of the alkaline earth metals include Be, Mg, Ca, Sr, Ba, and Ra. Examples of the transition metals include elements in the fourth series of the periodic table, such as Sc, Ti, V, Cr, Mn, Fe, Co, Ni, Cu, Zn, Ga, Ge, and As; elements in the fifth series, such as Y, Zr, Nb, Mo, Tc, Ru, Rh, Pd, Ag, Cd, In, Sn, and Sb; elements in the sixth series, such as La, Hf, Ta, W, Re, Os, Ir, Pt, Au, Hg, Tl, Pb, and Bi; and other elements, such as Al and Si.

The metal salts include hydrochlorides, nitrates, phosphates, carbonates, acetates, double salts comprising two or more salts, complex salts containing complex ions, which may be in a form of anhydride or hydrate.

Specific examples of the metal salts include $Ti(SO_4)_2$, $CuSO_4 \cdot 5H_2O$, $Zn(NO_3)_2 \cdot 6H_2O$, $Ca(NO_3)_2 \cdot 4H_2O$, $CaCl_2$, $MgCO_3$, $Fe_3(PO_4)_2$, and $Cu(CH_3COO)_2$; double salts, such as $KMgCl_3$ and $AlK(SO_4)_2$; and complex salts, such as $K_3[Fe(CN)_6]$ and $[CoCl(NH_3)_5]Cl_2$.

The metal salts may be used singly or as a mixture of two or more kinds. For example, in the case of using a mixture of a titanium salt and a zinc salt as starting materials, either a mixture of zinc oxide and titanium oxide, or a double salt, namely zinc titanate ($Zn_2TiO_4$), is produced depending upon the temperature conditions, and is used as particles for the matrix particles or the daughter particles.

As for the solvents for solutions of the metal salts, water or organic solvents can be used, with a preference given to the solvents which do not inhibit a drying process or a pyrolysis process of the starting material droplets. Examples of the organic solvents include alcohols, such as methanol and ethanol, and polar solvents, such as N,N-dimethyl formamide, dimethyl sulfoxide, and hexamethylphosphoramide.

Many of the fluorine compounds are chemically stable and have a low refractive index, so that the compounds are highly useful for controlling the refractive index of the resulting composite fine particles. The fluorine compounds include any ones in a solid or liquid state at room temperature. Examples of such solid inorganic fluorine compounds include $MgF_2$, $CaF_2$, $AlF_3$, $LiF$, $NiF_2$, and $BaF_2$. Examples of solid organic fluorine compounds include fluororesins, such as polytetrafluoroethylene (hereinafter simply abbreviated as "PTFE"), a tetrafluoroethylenehexafluoropropylene copolymer, a tetrafluoroethyleneethylene copolymer, vinylidene polyfluoride, and vinyl polyfluoride. Among them, $MgF_2$, polytetrafluoroethylene, and a mixture thereof are suitably used as the fluorine compounds from the viewpoint of having a suitable refractive index and good transparency in the resulting composite fine particles.

The average particle diameter of the fluorine compounds in a solid state at room temperature is preferably not more than 0.3 μm, more preferably not more than 0.2 μm. This is because when the average particle diameter exceeds 0.3 μm, the aggregating forces among the particles become weak, thereby lowering the hardness of the composite fine particles.

Examples of liquid fluorine compounds at room temperature include perfluoropolyethers (hereinafter simple abbreviated as "PFPE"). An example of PFPE may be perfluoropolymethylisopropylether (for instance, "FOMBLIN HC", manufactured by Nikko Chemicals K.K.). PFPE is useful not only for lowering the refractive index of the composite fine particles but also for providing moisture with smooth skin texture, so that the PFPE is highly suitable as fine particles for use in cosmetics. When the liquid fluorine compounds are used, the solvents used may be properly chosen in order not to cause phase separation of the daughter particle starting materials and the matrix particle starting materials in the solvent. However, when the solvent is water, an emulsion comprising liquid fluorine compounds at room temperature which are emulsified by various kinds of surfactants may be preferably used. For instance, an emulsion of perfluoropolyether (oil-in-water type) may be used. The emulsion diameter is preferably in a size not more than 0.1 times those of droplets. When the emulsion diameter exceeds 0.1 times those of the droplets, the emulsion becomes larger than the produced particles, and thereby the production of particles becomes difficult.

As explained above, in the present invention, the liquid fluorine compounds may be also used as materials having low refractive indices. In this case, the liquid fluorine compounds may be used together with the metal oxides and/or the solid fluorine compounds in order to increase freedom in the refractive index control.

As for suitable combinations of the daughter particles and the matrix particles in the present invention, a preference is given to the combinations where the daughter particles are selected from $TiO_2$, ZnO, and a mixture thereof, and the matrix particles are selected from $SiO_2$ and a mixture of $SiO_2$ with perfluoropolyether from the viewpoints of providing safety and stability of the resulting ultraviolet shielding agents.

In the present invention, materials other than the metal oxides and the fluorine compounds mentioned above may be included in the daughter particles and the matrix particles. For example, in the case where the composite fine particles are produced by atomize-drying a sol, stabilizers of the starting material sol or a coating agent for sol particles may be contained in the matrix particles as long as the optical properties of the composite fine particles are not impaired.

Next, the preparation of the starting material liquid mixture using the starting materials mentioned above and the method for producing the composite fine particles using the apparatus mentioned above will be explained in further detail below.

When the liquid mixture of the starting materials is prepared, it is important to uniformly blend the starting materials for the daughter particles and the starting materials for the matrix particles in order to give a uniformly blended mixture in which the daughter particles are well-dispersed in the matrix particles. Such a uniformly blended mixture in turn allows to disperse the daughter particles on the surface of the composite fine particles thus produced and/or in the inner portion of the composite fine particles.

As for the solvents for the starting materials for the daughter particles and the starting materials for the matrix particles mentioned above, water or organic solvents may be used, with a preference given to solvents which do not inhibit a drying process and a pyrolysis process of the starting material droplets. Examples of the organic solvents include alcohols, such as methanol and ethanol, and polar solvents, such as N,N-dimethylformamide, dimethyl sulfoxide, and hexamethylphosphoramide. As long as the production of the ultraviolet shielding composite fine particles is not affected in the drying process and/or in the pyrolysis process of the starting material droplets, the same or different solvents from the solvents for the metal salt solutions mentioned above may be used.

The concentration of the daughter particles in the starting material liquid mixture containing the starting materials for the daughter particles and the starting materials for the matrix particles is preferably in the range of from $10^{-5}$ to 10 mol/l, more preferably from $10^{-4}$ to 1 mol/l. This is because when the concentration of the daughter particles is lower than $10^{-5}$ mol/l, the amount of the daughter particles in the composite fine particles is extremely small, thereby making it difficult to achieve good optical properties of the daughter particles. On the other hand, when the concentration is higher than 10 mol/l, the specific gravity of the overall mixture excessively increases, thereby making it difficult to form fine liquid droplets.

The metal salt concentration in the starting material liquid mixture containing the starting materials for the daughter particles and the starting materials for the matrix particles is preferably in the range of from $10^{-5}$ to 20 mol/l, more preferably from $10^{-4}$ to 10 mol/l, This is because when the metal salt concentration is lower than $10^{-5}$ mol/l, the amount of the metal oxide fine particles produced is extremely small, and when the concentration is higher than 20 mol/l, the viscosity of the mixture becomes extremely high, thereby making it difficult to form droplets.

The concentration of the fluorine compounds in the starting material liquid mixture containing the starting materials for the daughter particles and the starting materials for the matrix particles is preferably in the range of from $10^{-5}$ to 20 mol/l, more preferably from $10^{-4}$ to 10 mol/l, This is because when the concentration of the fluorine compounds is lower than $10^{-5}$ mol/l, the amount of the fluorine compound fine particles produced is extremely small, and when the concentration is higher than 20 mol/l, the viscosity of the mixture becomes extremely high, thereby making it difficult to form droplets.

The droplets obtained from the above starting material liquid mixture have an average droplet diameter of from 0.1 to 2000 μm, preferably from 0.1 to 1000 μm, particularly preferably from 0.1 to 500 μm. Also, the distribution of the droplet diameter is preferably kept as narrow as possible. When the average droplet diameter is smaller than 0.1 μm or larger than 2000 μm, the formation of fine droplets would be difficult. Incidentally, the droplet diameter is preferably measured in a vapor-liquid mixed state. For instance, the droplet diameter can be determined by a device for measuring light scattering-type diameter distribution (for instance, LDSA-2300A, manufactured by Kuana-Giken Corp.).

The obtained droplets are supplied to the drying pipe or the reaction pipe by the carrier gas mentioned above to produce the ultraviolet shielding composite fine particles of the present invention through a drying process and/or a pyrolysis process. Here, as for the flow amount of the carrier gas, it is preferably controlled so that the retention time of the carrier gas containing the starting material droplets in the drying pipe or the reaction pipe should not be shortened to less than 1 second. Also, the temperature of the drying pipe or the reaction pipe may be suitably set depending upon the kinds of the starting materials and the solvents, and the temperature is preferably in the range of 100° to 1500° C., more preferably 100° to 1000° C. When the temperature of the drying pipe or the reaction pipe is less than 100° C., the drying speed and/or the pyrolysis reaction speed are drastically lowered, so that the production of particles is likely to be difficult, and when the temperature exceeds 1500° C., the solvents drastically evaporate, making it undesirably difficult to control the shapes of the particles and the particle diameter.

The ultraviolet shielding composite fine particles of the present invention can be obtained by the production method explained above, and the ultraviolet shielding composite fine particles have a structure that the matrix particles comprise aggregates of primary particles, which are formed while retaining the shapes of the primary particles, each primary particle being aggregated in a closest state, and that the daughter particles are dispersed on the surface and in the inner portion of the matrix particles. When the dispersability of the daughter particles is poor, the optical properties of the daughter particles cannot be well exhibited. When the daughter particles are present on the surface of the matrix particles, the ultraviolet light which collides with the daughter particles is partially absorbed while the remaining ultraviolet light is externally scattered from the composite fine particles. The ultraviolet light which does not collide with the daughter particles on the surface and further enters into the inner portion of the matrix particles is subject to absorption and scattering by the daughter particles contained in the inner portion of the matrix particles, so that the ultraviolet light is effectively shielded.

The sizes and shapes of the matrix particles in the present invention, namely those of the composite fine particles, are not particularly limited. Depending upon the applications thereof, various sizes of, for instance, spherical forms, etc. of the composite fine particles can be used. For instance, as cosmetic powders, spherical particles having a particle diameter of 1 to 10 µm are preferably used from the viewpoints of having smooth skin texture and providing easy handling.

The ultraviolet shielding composite fine particles produced in the present invention have a particle diameter of from 0.01 to 500 µm by adjusting the starting material liquid mixture concentration in the atomized droplets. Particularly in order to provide easy handling of the composite fine particles, the particle diameter of the composite fine particles is preferably in the range of from 0.1 to 500 µm, more preferably from 0.5 to 100 µm, particularly from 1 to 50 µm. When the particle diameter of the composite fine particles is less than 0.1 µm, the surface treatment of the composite fine particles is liable to be too complicated, and when it exceeds 500 µm, the particles are too large to be used for cosmetics, making it difficult to disperse a large number of the composite fine particles in a medium, so that the advantageous effects for ultraviolet shielding are not likely to be achieved. The particle diameter may be measured by various methods, including, for instance, a scanning-type or transmission-type electron microscope.

The amount of the daughter particles in the composite fine particles is not particularly limited as long as the daughter particles can be well dispersed in the matrix particles without causing excess aggregation of the daughter particles in the composite fine particles. The amount of the daughter particles contained in the composite fine particles is normally in an amount of 0.1 to 50% by volume, preferably 0.1 to 30% by volume, more preferably 0.5 to 20% by volume. In the case where the metal oxides and the fluorine compounds are contained in the matrix particles, the amount of the fluorine compounds is at least not less than 1% by weight.

The optical properties of the ultraviolet shielding composite fine particles of the present invention can be quantitatively evaluated by measuring light transmittance by an ultraviolet-visible light spectrophotometer.

The preferred ultraviolet shielding ability for the composite fine particles of the present invention in a medium having substantially the same refractive index as the refractive index of the composite fine particles is a light transmittance of not less than 90% at a wavelength of 800 nm, a light transmittance of not less than 40% at a wavelength of 400 nm, and a light transmittance of not more than 5% at one or more of the wavelengths of 320 nm, 320 nm, and 300 nm, as measured by an ultraviolet-visible light spectrophotometer using an optical cell having an optical path length of 1 mm. By having the above optical properties, a high light transmittance particularly in the visible light region as well as a high shielding ability in the ultraviolet region can be satisfactorily achieved. Incidentally, "a medium having substantially the same refractive index as the refractive index of the composite fine particles" means that the difference in the refractive indices between a sample of the composite fine particles and the medium is within ±0.1, preferably within ±0.05.

The ultraviolet shielding ability mentioned above can be evaluated by an ultraviolet-visible light spectroscopy detailed below.

The composite fine particles are suspended in a medium having substantially the same refractive index as the refractive index of the composite fine particles to prepare a suspension of composite fine particles having a given concentration. In order to prepare a uniform suspension, the composite fine particles are stirred and well dispersed using, for instance, an ultrasonic disperser, etc. An optical cell having an optical path length of 1 mm is filled with the above suspension. An optical cell used herein has no absorption or no scattering of the light in the ultraviolet region and the visible light region, and, for instance, a silica cell can be used therefor. The light transmittance through the optical cell is measured using an ultraviolet-visible light spectrophotometer (for instance, UV-160A, manufactured by Shimadzu Corp.). In this method, the other optical cell filled with a medium without suspending the composite fine particles is used as a control to remove background.

The ultraviolet shielding composite fine particles of the present invention may be suitably subject to a hydrophobic treatment depending upon cosmetics incorporated therein.

Examples of the hydrophobic treatment methods include treatments with silicone compounds, such as methyl hydrogen polysiloxane, high-viscosity silicone oils, and silicone resins; treatments with surfactants, such as anionic surfactants and cationic surfactants; treatments with macromolecular compounds, such as nylon, polymethylmethacrylate, polyethylene, Teflon™, and polyamino acids; treatments with perfluoro-group containing compounds, lecithin, collagen, metal soaps, lipophilic waxes, esters of polyhydric alcohols. In general, any treatment methods suitable for the hydrophobic treatment of powders may be employed, and they are not limited to the above methods.

The cosmetics of the present invention may be prepared by optionally blending various kinds of adjuncts conventionally used for cosmetics in addition to the above ultraviolet shielding composite fine particles, if necessary. Examples of the cosmetic adjuncts are given below.

(1) Inorganic powders such as talc, kaolin, sericite, muscovite, phlogopite, lepidolite, biotite, synthetic golden mica, vermiculite, magnesium carbonate, calcium carbonate, diatomateous earth, magnesium silicate, calcium silicate, aluminum silicate, barium silicate, barium sulfate, strontium silicate, metallic tungustates, silica, hydroxylapatite, zeolite, boron nitride, and ceramic powders.

(2) Organic powders such as nylon powders, polyethylene powders, polystyrene powders, benzoguanamine resin powders, polytetrafluoroethylene powders, distyrenebenzenepolymer powders, epoxy resin powders, acrylic resin powders, and fine crystalline cellulose.

(3) Inorganic white pigments such as titanium oxide and zinc oxide; inorganic red pigments such as iron oxide (red oxide) and iron titanate; inorganic brown pigments such as γ-iron oxide; inorganic yellow pigments such as yellow iron oxide and yellow ochre; inorganic black pigments such as black iron oxide and carbon black; inorganic violet pigments such as manganese violet and cobalt violet; inorganic green pigments such as chromium oxide, chromium hydroxide, and cobalt titanate; inorganic blue pigments such as ultramarine and Prussian blue; pearl-like pigments such as mica coated with titanium oxide, oxychlorobismuth coated with titanium oxide, oxychlorobismuth, talc coated with titanium oxide, fish scale flake, mica coated with colored titanium oxide; and metal powder pigments such as aluminum powders and copper powders.

(4) Organic pigments including Pigment Red 57-1, Pigment Red 57, Pigment Red 53 (Ba), Pigment Red 49 (Na), Pigment Red 63 (Ca), Vat Red 1, Pigment Red 4, Pigment Red 48, Pigment Orange 5, Pigment Orange 13, Pigment Yellow 12, Pigment Yellow 1, and Pigment Blue 15; organic pigments including zirconium lakes, barium lakes, and aluminum lakes of Acid Red 51, Acid Red 92, Acid Red 52, Acid Red 33, Acid Red 87, Acid Violet 9, Solvent Orange 7, Acid Orange 7, Acid Yellow 23, Acid Yellow 5, Acid Yellow 73, Acid Yellow 3, Food Green 3, and Food Blue 1.

(5) Natural pigments such as chlorophyll and β-carotene.

(6) Various hydrocarbons, higher fatty acids, fats and oils, esters, higher alcohols, and waxes, such as squalane, paraffin wax, liquid paraffin, Vaseline™, microcrystalline wax, ozocerite, ceresine, myristic acid, palmitic acid, stearic acid, oleic acid, isostearic acid, cetyl alcohol, hexadecyl alcohol, oleyl alcohol, cetyl 2-ethylhexanoate, 2-ethylhexyl palmitate, 2-octyldodecyl myristate, neopentyl glycol di-2-ethylhexanoate, glycerol tri-2-ethylhexanoate, 2-octyldodecyl oleate, isopropyl myristate, glycerol triisostearate, coconut fatty acid triglyceride, olive oil, avocado oil, camellia oil, jojoba oil, beeswax, spermaceti, carnauba wax, myristyl myristate, mink oil, and lanoline; silicone oils such as volatile silicone oils and non-volatile silicone oils.

(7) The ultraviolet protecting agents such as ultraviolet light absorbents may be optionally added, if necessary. Examples of the ultraviolet light absorbents include the following:

(a) Benzoic acid derivatives including p-aminobenzoic acid (PABA), glycerol mono-p-aminobenzoate, ethyl p-N,N-dipropoxyaminobenzoate, ethyl p-N,N-diethoxyaminobenzoate, ethyl p-N,N-dimethylaminobenzoate, butyl p-N,N-dimethylaminobenzoate, amyl p-N,N-dimethylaminobenzoate, and octyl p-N,N-dimethylaminobenzoate.

(b) Anthranilic acid derivatives including homomenthyl N-acetylanthranilate.

(c) Salicylic acid derivatives including amyl salicylate, menthyl salicylate, homomenthyl salicylate, octyl salicylate, phenyl salicylate, benzyl salicylate, and p-isopropanolphenyl salicylate.

(d) Cinnamic acid derivatives including octylcinnamate, ethyl 4-isopropylcinnamate, methyl 2,5-diisopropyl cinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, 2-ethylhexyl α-cyano-β-phenylcinnamate, and glycerol mono-2-ethylhexanoyl-diparamethoxycinnamate.

(e) Benzophenone derivatives including 2,4-dihydroxybenzophenone, 2,2'-dihydroxy 4-methoxybenzophenone, 2,2'-dihydroxy 4,4'-dimethoxybenzophenone, 2,2',4,4'-tetrahydroxy. benzophenone, 2-hydroxy 4-methoxybenzophenone, 2-hydroxy 4-methoxy-4'-methylbenzophenone, 2-hydroxy 4-methoxybenzophenone-5-sulfonate, 4-phenylbenzophenone, 2-ethylhexyl 4'-phenylbenzophenone-2-carboxylate, 2-hydroxy 4-n-octoxybenzophenone, and 4-hydroxy 3-carboxybenzophenone.

(f) Other ultraviolet absorbents include: 3-(4'-methylbenzylidene) d,1-camphor, 3-benzylidene d,1-camphor, urocanic acid, ethyl urocanate, 2-phenyl 5-methylbenzoxazole, 2,2'-hydroxy 5-methylphenylbenzotriazole, 2-(2'-hydroxy-5't-octylphenyl)benzotriazole, dibenzarsine, dianisoylmethane, 4-methoxy 4'-t-butyldibenzoylmethane, 5-(3,3'-dimethyl-2-norbornylidene)-3-pentane-2-one, and 1-(3,4-dimethoxyphenyl)-4,4'-dimethyl-1,3-pentadione.

(8) Also, surfactants may be optionally used, if necessary. Examples of the surfactants include polyoxyethylene alkyl ethers, polyoxyethylene fatty acid esters, polyoxyethylene sorbitan fatty acid esters, polyoxyethylene sorbitol fatty acid esters, alkyl polyoxyethylene hardened castor oil sulfates, alkyl polyoxyethylene sulfates, alkyl phosphates, alkyl polyoxyethylene phosphates, alkali metal salts of fatty acids, sorbitan fatty acid esters, and glycerol fatty acid esters.

(9) Further, water-soluble polyhydric alcohols may be optionally used. Examples of the water-soluble polyhydric alcohols are water-soluble polyhydric alcohols having two or more hydroxyl groups in a molecule, including ethylene glycol, propylene glycol, 1,3-butylene glycol, 1,4-butylene glycol, dipropylene glycol, glycerol, polyglycerols, such as diglycerol, triglycerol, and tetraglycerol, glucose, maltose, maltitol, sucrose, fructose, xylitol, sorbitol, maltotriose, threitol, erythritol, and sugar alcohol derived from decomposed starch.

(10) In addition, other cosmetic adjuncts may be optionally added, including amino acids, such as lysine and arginine; organic acids, such as lactic acid, citric acid, succinic acid, and glycolic acid, and organic salts thereof; resins, such as alkyd resins and urea resins; plasticizers, such as camphor and tributyl citrate; antioxidants, such as α-tocopherol; antiseptics, such as butyl p-hydroxybenzoate and methyl p-hydroxybenzoate; extracts from plants, such as cornflower, althea, and *Hypericuor erectum;* bioactive substances such as retinol and allantoin; binders such as xantane gum and carrageenan; and perfumes.

Although an amount of the ultraviolet shielding composite fine particles of the present invention depends upon the kinds of cosmetics produced, the amount is preferably 0.1 to 60% by weight, more preferably 0.2 to 40% by weight, particularly 0.5 to 30% by weight. When the amount of the ultraviolet shielding composite fine particles is less than 0.1% by weight, sufficient shielding effects against the ultraviolet light cannot be achieved, and when the amount exceeds 60% by weight, a further addition of the composite fine particles shows no additional effects, and the costs thereof are merely increased.

The cosmetics of the present invention may be formulated in various forms as conventionally prepared. Although the forms are not particularly limited, the cosmetics may be formulated as various make-up products, including lotions, emulsions, creams, ointments, aerosol cosmetics, powdery foundations, powdery eyeshadows, emulsified foundation creams, and lipsticks.

The present invention will be hereinafter explained in more detail by means of the following examples, without intending to limit the scope of the present invention thereto.

EXAMPLE 1

73.3 g of a silica sol ("ST-C," manufactured by Nissan Chemical Industries, Ltd.; $SiO_2$ concentration: 20.5% by weight) and 25.0 g of a titanium oxide sol ("TITANIA SOL," manufactured by Taki Chemical Co., Ltd.; anatase-type; $TiO_2$ concentration: 4% by weight) are mixed. To the mixture, water is added to make up a volume of 1 liter, yielding a starting material liquid mixture. Specifically, the concentrations of $SiO_2$ and $TiO_2$ in the starting material liquid mixture are, respectively, 0.25 mol/liter and 0.0125 mol/liter, and the amount of the daughter-and-matrix particle mixture contained in the above starting material liquid mixture is 1.6% by weight.

In order to improve the dispersability of the fine particles in the above starting material liquid mixture and to get a uniform blend of these fine particles, the starting material liquid mixture is stirred for a given period of time, and then the mixture is subject to an ultrasonic dispersion treatment for about 30 minutes. The dispersed starting material liquid mixture is then atomized with an ultrasonic nebulizer ("NE-U12," manufactured by Omron Corporation, to give fine droplets having an average particle diameter of about 5 μm. The formed droplets are carried along with a nitrogen carrier gas having a flow rate controlled at 4 liter/minute, so as to pass the formed droplets through a ceramic drying pipe heated externally at 150° C. by an electric furnace ("MULLITE TUBE," manufactured by Nikkato Corporation; an inner diameter of 60 mm and a tubular length of 750 mm). In the ceramic drying pipe, the formed droplets are dried to give fine particles. The formed composite fine particles dispersed in a nitrogen carrier gas are then collected by a diffusion charging-type electrostatic collector.

The obtained particles are white, showing a smooth skin texture. The particles are observed by a scanning electron microscope (JSM-T100, manufactured by JEOL (Nihon Denshi Kabushiki Kaisha)). As a result, it is found that the particles are spherical particles having an average particle diameter of about 1 μm. Also, a cross section of the particles is observed by a transmission electron microscope (JEM-2000FX, manufactured by JEOL) using an ultrathin sectioning method. Consequently, it is found that $TiO_2$ ultrafine particles (average particle diameter: about 0.01 μm) are dispersed in and supported by aggregates of $SiO_2$ ultrafine particles (average particle diameter: about 0.01 μm). In other words, the composite fine particles are $TiO_2/SiO_2$ composite fine particles; matrix particles are the aggregates of $SiO_2$ particles having a band gap energy of about 6.2 eV and a refractive index of about 1.46; and daughter particles are $TiO_2$ particles having a band gap energy of about 3.4 eV and a refractive index of about 2.52 (anatase-type).

The amount of the daughter particles in the above composite fine particles is about 3.8% by volume, and the specific surface area of the composite fine particles as determined by the BET method is about 230 $m^2/g$. Here, the amount of the daughter particles is calculated from the compositional ratio of particles in the starting material liquid mixture, wherein particle densities of $SiO_2$ and $TiO_2$ are 2.27 $g/cm^3$ and 3.84 $g/cm^3$, respectively, and these values are used for the calculation.

Figure 2:
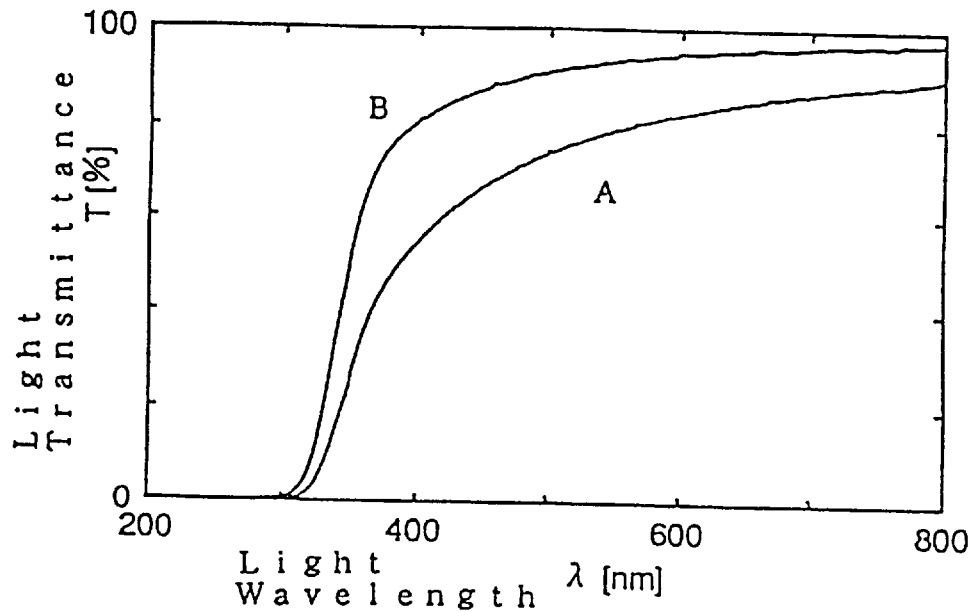
FIG. 2 is a graph showing the relationship between a light wavelength and a light transmittance of the ultraviolet shielding composite fine particles obtained in Examples 1 and 2, as measured by an ultraviolet-visible light spectrophotometer, wherein "A" refers to Example 1, and "B" refers to Example 2.

The refractive index of the composite fine particles is about 1.5, as calculated from the volume ratio of the matrix particles to the daughter particles. Twenty mg of the composite fine particles having the above refractive index are suspended in glycerol (refractive index: 1.47) used as a dispersion medium for the composite fine particles to prepare 2 g of glycerol suspension in which 1% by weight of the composite fine particles is suspended. The light transmittance of the obtained suspension is evaluated by an ultraviolet-visible light spectrophotometer (UV-160A, manufactured by Shimadzu Corporation). Here, the light transmittance is measured using a silicious cell having an optical path length of 1 mm in a wavelength of from 200 to 800 nm. The results are shown in FIG. 2 (denoted by "A").

In the figure, the light transmittance of the composite fine particles is substantially equal to 0% in the ultraviolet region B and the ultraviolet region C, the wavelengths of which are not longer than 300 nm. At the same time, the composite fine particles show remarkably high light transmittance values in the entire visible light region at a wavelength of from 400 to 800 nm, as is seen from the results that the light transmittance at 400 nm is 55%, and the light transmittance at 800 nm is 91%. Accordingly, the composite fine particles thus produced have a high transparency in the visible light region and a high shielding ability in the ultraviolet region.

EXAMPLE 2

A silica sol ("ST-C," manufactured by Nissan Chemical Industries, Ltd.; $SiO_2$ concentration: 20.5% by weight) and a titanium oxide sol ("TITANIA SOL," manufactured by Taki Chemical Co., Ltd.; anatase-type; $TiO_2$ concentration: 4% by weight) are mixed in the same amounts as in Example 1 together with 2.31 g of an oil-in-water emulsion ("FOMBLIN HC/04, base (NET FB04)," manufactured by Nikko Chemicals, Ltd.) of PFPE (perfluoropolyether). To the mixture, water is added to make up a volume of 1 liter, yielding a starting material liquid mixture. Here, the oil-in-water emulsion has an average diameter of about 0.26 μm and an emulsion concentration of 65% by weight. Specifically, the concentrations of $SiO_2$, $TiO_2$, and PFPE in the starting material liquid mixture are, respectively, 0.25 mol/liter, 0.0125 mol/liter, and 0.001 mol/liter, and the amount of the daughter-and-matrix particle mixture contained in the above starting material liquid mixture is 1.75% by weight.

The obtained starting material liquid mixture is subject to a dispersion treatment in the same manner as in Example 1. In subsequent to the dispersion treatment, the starting material liquid mixture is atomized to produce droplets in the same manner as in Example 1. The formed droplets are then dried in the same manner as in Example 1, to give composite fine particles comprising matrix particles (the aggregates of a mixture of $SiO_2$ particles and PFPE), and daughter particles ($TiO_2$ particles).

The resulting particles are white and have a smooth skin texture with moisture. The shapes of the composite fine particles are observed by methods similar to those in Example 1. As a result, it is found that the composite fine particles are spherical particles having an average particle diameter of about 1 μm, wherein $TiO_2$ ultrafine particles (average particle diameter: about 0.01 μm) are dispersed in and supported by aggregates of a mixture of $SiO_2$ ultrafine particles (average particle diameter: about 0.01 μm) and PFPE. In other words, the composite fine particles are $TiO_2$/(PFPE, $SiO_2$) composite fine particles; matrix particles are the aggregates comprising a mixture of $SiO_2$ particles and PFPE (refractive index: about 1.29); and daughter particles are $TiO_2$ particles.

The amount of the daughter particles in the above composite fine particles is about 3.4% by volume, and the specific surface area of the composite fine particles as determined by the BET method is about 90 $m^2/g$. Here, the amount of the daughter particles is calculated from the compositional ratio of particles in the starting material liquid mixture, wherein particle densities of $SiO_2$, $TiO_2$, and PFPE, are 2.27 $g/cm^3$, 3.84 $g/cm^3$, and 1.87 $g/cm^3$, respectively, and these values are used for the calculation.

The refractive index of the composite fine particles is about 1.48, as calculated from the volume ratio of the matrix particles to the daughter particles. Twenty mg of the composite fine particles having the above refractive index are suspended in glycerol (refractive index: 1.47) used as a dispersion medium for the composite fine particles to prepare 2 g of glycerol suspension in which 1% by weight of the composite fine particles is suspended. The light transmittance of the obtained suspension is evaluated in the same manner as in Example 1. The results are shown in FIG. 2 (denoted by "B").

In the figure, the light transmittance of the composite fine particles is substantially equal to 0% in the ultraviolet region B and the ultraviolet region C, the wavelengths of which are not longer than 300 nm. At the same time, the composite fine particles show remarkably high light transmittance values in the entire visible light region at a wavelength of from 400 to 800 nm, as is seen from the results that the light transmittance at 400 nm is 81%, and the light transmittance at 800 nm is 98%. Accordingly, the composite fine particles thus produced have a high transparency in the visible light region and a high shielding ability in the ultraviolet region.

EXAMPLE 3

A silica sol ("ST-C," manufactured by Nissan Chemical Industries, Ltd.; $SiO_2$ concentration: 20.5% by weight) and a titanium oxide sol ("TITANIA SOL," manufactured by Taki Chemical Co., Ltd.; anatase-type; $TiO_2$ concentration: 4% by weight) are mixed in the same amounts as in Example 1 together with 9.24 g of an oil-in-water emulsion ("FOMBLIN HC/04, base (NET FB04)," manufactured by Nikko Chemicals, Ltd.) of PFPE. To the mixture, water is added to make up a volume of 1 liter, yielding a starting material liquid mixture. Here, the oil-in-water emulsion has an average diameter of about 0.26 μm and an emulsion concentration of 65% by weight. Specifically, the concentrations of $SiO_2$, $TiO_2$, and PFPE in the starting material liquid mixture are, respectively, 0.25 mol/liter, 0.0125 mol/liter, and 0.004 mol/liter, and the amount of the daughter-and-matrix particle mixture contained in the above starting material liquid mixture is 2.2% by weight.

The obtained starting material liquid mixture is subject to a dispersion treatment in the same manner as in Example 1.

In subsequent to the dispersion treatment, the starting material liquid mixture is atomized to produce droplets in the same manner as in Example 1. The formed droplets are then dried in the same manner as in Example 1, to give composite fine particles comprising matrix particles (aggregates of a mixture of $SiO_2$ particles and PFPE), and daughter particles ($TiO_2$ particles).

The resulting particles are white and have a smooth skin texture having superior moisture to those obtained in Example 2. The shapes of the composite fine particles are observed by a method similar to that in Example 1. As a result, it is found that the composite fine particles are spherical particles having an average particle diameter of about 1 μm, wherein $TiO_2$ ultrafine particles (average particle diameter: about 0.01 μm) are dispersed in and supported by aggregates of a mixture of $SiO_2$ ultrafine particles (average-particle diameter: about 0.01 μm) and PFPE. In other words, the composite fine particles are $TiO_2$/(PFPE, $SiO_2$) composite fine particles; matrix particles are the aggregates comprising a mixture of $SiO_2$ particles and PFPE; and daughter particles are $TiO_2$ particles.

The amount of the daughter particles in the above composite fine particles is about 2.6% by volume, and the specific surface area of the composite fine particles as determined by the BET method is about 46 $m^2/g$. Here, the amount of the daughter particles is calculated in the same manner as in Example 2.

Figure 3:
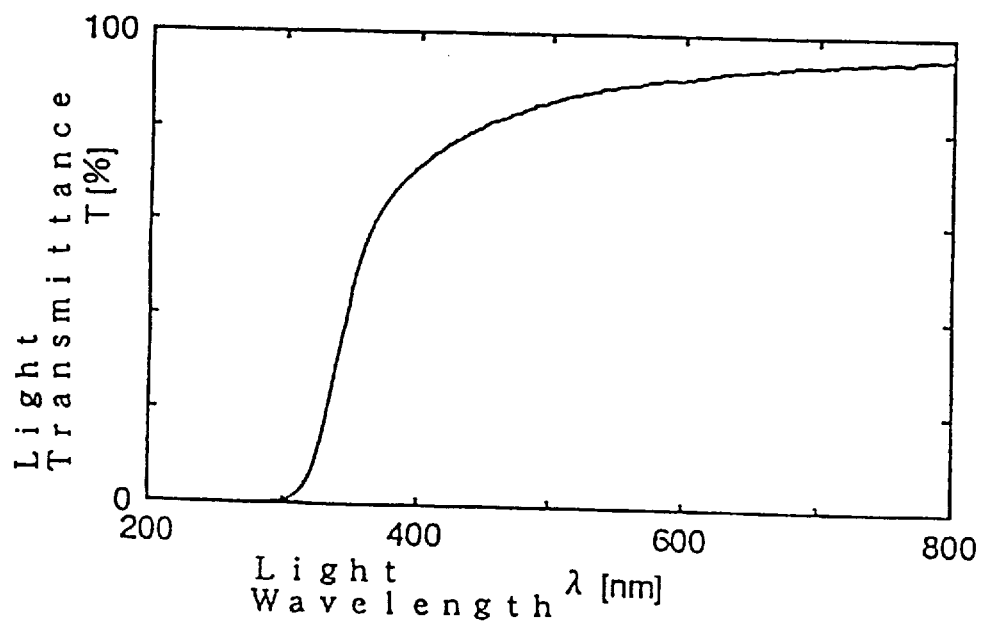
FIG. 3 is a graph showing the relationship between a light wavelength and a light transmittance of the ultraviolet shielding composite fine particles obtained in Example 3, as measured by an ultraviolet-visible light spectrophotometer.

The refractive index of the composite fine particles is about 1.44, as calculated from the volume ratio of the matrix particles to the daughter particles. So, malic distearyl ("COSMOL 222," manufactured by The Nisshin Oil Mills, Ltd.; refractive index: 1.46) is used as a dispersion medium for the composite fine particles. The light transmittance of the malic distearyl suspension in which 1% by weight of the composite fine particles is suspended is evaluated in the same manner as in Example 1. The results are shown in FIG. 3.

In the figure, the light transmittance of the composite fine particles is substantially equal to 0% in the ultraviolet region B and the ultraviolet region C, the wavelengths of which are not longer than 300 nm. At the same time, the composite fine particles show remarkably high light transmittance values in the entire visible light region at a wavelength of from 400 to 800 nm, as is seen from the results that the light transmittance at 400 nm is 72%, and the light transmittance at 800 nm is 96%. Accordingly, the composite fine particles thus produced have a high transparency in the visible light region and a high shielding ability in the ultraviolet region.

EXAMPLE 4

73.3 g of a silica sol ("ST-C," manufactured by Nissan Chemical Industries, Ltd.; $SiO_2$ concentration: 20.5% by weight), and 0.814 g of zinc oxide ultrafine particles ("FINEX 75," manufactured by Sakai Chemical. Industry Co., Ltd.) are mixed. To the mixture, water is added to make up a volume of 1 liter, yielding a starting material liquid mixture. Specifically, the concentrations of $SiO_2$ and ZnO in the starting material liquid mixture are, respectively, 0.25 mol/liter and 0.01 mol/liter, and the amount of the daughter-and-matrix particle mixture contained in the above starting material liquid mixture is 1.58% by weight.

The starting material liquid mixture is then subject to a dispersion treatment using a high-pressure disperser ("LA31," manufactured by Nanomizer Inc.) under the conditions of a pressure of 1300 $kgf/cm^2$ and a number of passing times of 10 times. Drying is then carried out in the same manner as in Example 1 except that air is used as a carrier gas, and the set temperature of the drying tube is 500° C., to produce composite fine particles comprising matrix particles (aggregates of $SiO_2$ particles) and daughter particles (ZnO particles).

The obtained particles are white, showing a smooth skin texture. The shapes of the composite fine particles are observed in the same manner as in Example 1. As a result, it is found that the particles are spherical particles having an average particle diameter of about 1 μm. Also, it is found that ZnO ultrafine particles (average particle diameter: about 0.01 μm) are dispersed in and supported by aggregates of $SiO_2$ ultrafine particles (average particle diameter: about 0.01 μm). In other words, the composite fine particles are $ZnO/SiO_2$ composite fine particles; matrix particles are the aggregates of $SiO_2$ particles having a band gap energy of about 6.2 eV and a refractive index of about 1.46; and daughter particles are ZnO particles having a band gap energy of about 3.2 eV and a refractive index of about 1.99.

The amount of the daughter particles in the above composite fine particles is about 2.1% by volume, and the specific surface area of the fine particles as determined by the BET method is about 160 $m^2/g$. Here, the amount of the daughter particles is calculated from the compositional ratio of particles in the starting material liquid mixture, wherein particle densities of $SiO_2$ and ZnO (wurtzite-type), are 2.27 $g/cm^3$ and 5.78 $g/cm^3$, respectively, and these values are used for the calculation.

Since the refractive index of the composite fine particles is about 1.47, as calculated from the volume ratio of the matrix particles to the daughter particles, malic distearyl is used as a dispersion medium. One-hundred twenty mg of the composite fine particles having the above refractive index are suspended in malic distearyl solution ("COSMOL 222," manufactured by The Nisshin Oil Mills, Ltd.; refractive index: 1.46), to prepare 2 g of malic distearyl suspension, in which 6% by weight of the composite fine particles is suspended. The light transmittance of the obtained suspension is evaluated in the same manner as in Example 1. The results are shown in FIG. 4.

In the figure, the light transmittance of the composite fine particles is substantially equal to 0% in the ultraviolet region A, the ultraviolet region B, and the ultraviolet region C, the wavelengths of which are not longer than 320 nm. At the same time, the composite fine particles show remarkably high light transmittance values in the entire visible light region at a wavelength of from 400 to 800 nm, as is seen from the results that the light transmittance at 400 nm is 90%, and the light transmittance at 800 nm is almost 100%. Accordingly, the composite fine particles thus produced have a high transparency in the visible light region and a high shielding ability in the ultraviolet region.

EXAMPLE 5

148 g of a magnesium fluoride sol ("MFS-10," manufactured by Nissan Chemical Industries, Ltd.; $MgF_2$ concentration: 10.5% by weight), and 1.00 g of titanium oxide ultrafine particles ("TTO-51(A)," manufactured by Ishihara Sangyo Kaisha, Ltd.; rutile-type) are mixed. To the mixture, water is added to make up a volume of 1 liter, yielding a starting material liquid mixture. Specifically, the concentrations of $MgF_2$ and $TiO_2$ in the starting material liquid mixture are, respectively, 0.25 mol/liter and 0.0125 mol/liter, and the amount of the daughter-and-matrix particle mixture contained in the above starting material liquid mixture is 1.66% by weight.

Next, glass beads (average particle diameter: 0.1 mm) are added to the above starting material liquid mixture to give a weight ration of the starting material liquid mixture to the glass beads of 175:325. The resulting mixture is subject to a dispersion treatment for 6 hours using a beads mill ("TSG-6H, " manufactured by Igarashi Kikai) at a blade rotational speed of 2000 r.p.m. After removal of the glass beads from the above mixture, drying is carried out. In the same manner as in Example 1 except that air is used as a carrier gas, and that the set temperature of the drying tube is 850° C., to produce composite fine particles comprising matrix particles (aggregates of $MgF_2$ particles) and daughter particles ($TiO_2$ particles).

The obtained particles are white, showing slightly smooth skin texture. The particles are observed in the same manner as in Example 1. As a result, it is found that the particles are spherical particles having an average particle diameter of about 1 μm. Also, it is found that $TiO_2$ ultrafine particles (average particle diameter: about 0.01 μm) are dispersed in and supported by aggregates of $MgF_2$ ultrafine particles (average particle diameter: about 0.02 μm). In other words, the composite fine particles are $TiO_2/MgF_2$ composite fine particles; matrix particles are the aggregates of $MgF_2$ particles having a band gap energy of about 6 eV and a refractive index of about 1.38; and daughter particles are $TiO_2$ particles having a band gap energy of about 3.3 eV and a refractive index of about 2.71.

The amount of the daughter particles in the above composite fine particles is about 5.0% by volume, and the specific surface area of the composite fine particles as determined by the BET method is about 130 $m^2/g$. Here, the amount of the daughter particles is calculated from the compositional ratio of particles in the starting material liquid mixture, wherein particle densities of $MgF_2$ and $TiO_2$ are 3.15 $g/cm^3$ and 3.84 $g/cm^3$, respectively, and these values are used for the calculation.

Since the refractive index of the composite fine particles is about 1.45, as calculated from the volume ratio of the matrix particles to the daughter particles, 20 mg of the composite fine particles having the above refractive index is suspended in ethylene glycol (refractive index: 1.43) used as a dispersion medium for the composite fine particles, to prepare 2 g of ethylene glycol suspension in which 1% by weight of the composite fine particles is suspended. The light transmittance of the obtained suspension is evaluated in the same manner as in Example 1. The results are shown in FIG. 5.

In the figure, the light transmittance of the composite fine particles is substantially equal to 0% in the ultraviolet region A, the ultraviolet region B, and the ultraviolet region C, the wavelengths of which are not longer than 340 nm. At the same time, the composite fine particles show remarkably high light transmittance values in the entire visible light region at a wavelength of from 400 to 800 nm, as is seen from the results that the light transmittance at 400 nm is 60%, and the light transmittance at 800 nm is 98%. Accordingly, the composite fine particles thus produced have a high transparency in the visible light region and a high shielding ability in the ultraviolet region.

EXAMPLE 6

Fifteen g of PTFE (polytetrafluoroethylene, LUBRON L5, manufactured by Daikin Industries, Ltd.; average particle diameter: 0.2 μm), and 0.814 g of zinc oxide ultrafine particles ("FINEX 75," manufactured by Sakai Chemical Industry Co., Ltd.) are mixed. To the mixture, water is added to make up a volume of 1 liter, yielding a starting material liquid mixture. Specifically, the concentrations of PTFE and ZnO in the starting material liquid mixture are, respectively, $1.0 \times 10^{-4}$ mol/liter and 0.01 mol/liter, and the amount of the daughter-and-matrix particle mixture contained in the above starting material liquid mixture is 1.58% by weight.

The starting material liquid mixture is subject to a dispersion treatment using a high-pressure disperser in the same manner as in Example 4. Drying is then carried out in the same manner as in Example 1 except that air is used as a carrier gas, and the set temperature of the drying tube is 200° C., to produce composite fine particles comprising matrix particles (aggregates of PTFE particles) and daughter particles (ZnO particles).

The obtained particles are white, showing slightly smooth skin texture. The particles are observed in the same manner as in Example 1. As a result, it is found that the particles are spherical particles having an average particle diameter of about 1 μm. Also, it is found that the ZnO ultrafine particles (average particle diameter: about 0.01 μm) are dispersed in and supported by aggregates of the PTFE fine particles (average particle diameter: about 0.2 μm). In other words, the composite fine particles are ZnO/PTFE composite fine particles; matrix particles are the aggregates of PTFE particles having a refractive index of about 1.41; and daughter particles are ZnO particles.

The amount of the daughter particles in the above composite fine particles is about 2.0% by volume, and the specific surface area of the composite fine particles as determined by the BET method is about 85 m$^2$/g. Here, the amount of the daughter particles is calculated from the compositional ratio of particles in the starting material liquid mixture, wherein a particle density of ZnO is 5.78 g/cm$^3$ and a density of PTFE is 2.2 g/cm$^3$, and these values are used for calculation.

Figure 6:
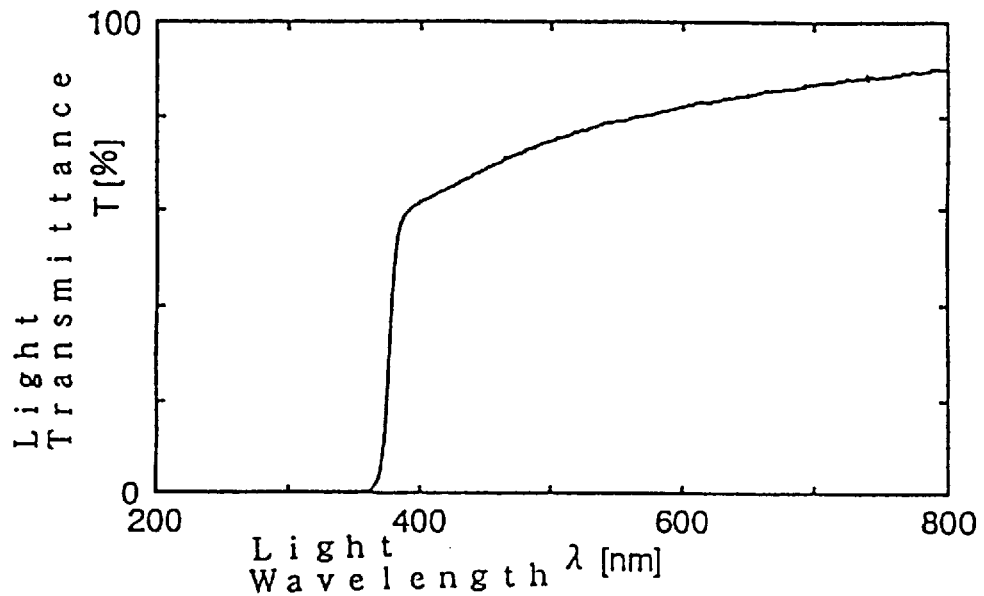
FIG. 6 is a graph showing the relationship between a light wavelength and a light transmittance of the ultraviolet shielding composite fine particles obtained in Example 6, as measured by an ultraviolet-visible light spectrophotometer.

Since the refractive index of the composite fine particles is about 1.42, as calculated from the volume ratio of the matrix particles to the daughter particles, ethylene glycol (refractive index: 1.43) is used as a dispersion medium for the composite fine particles. Specifically, 120 mg of the composite fine particles having the above refractive index is suspended in ethylene glycol, to prepare 2 g of ethylene glycol suspension in which 6% by weight of the composite fine particles. The light transmittance of the obtained suspension is evaluated in the same manner as in Example 1. The results are shown in FIG. 6.

In the figure, the light transmittance of the composite fine particles is substantially equal to 0% in the ultraviolet region A, the ultraviolet region B, and the ultraviolet region C, the wavelengths of which are not longer than 320 nm. At the same time, the composite fine particles show remarkably high light transmittance values in the entire visible light region at a wavelength of from 400 to 800 nm, as is seen from the results that the light transmittance at 400 nm is 62%, and the light transmittance at 800 nm is 90%. Accordingly, the composite fine particles thus produced have a high transparency in the visible light region and a high shielding ability in the ultraviolet region.

EXAMPLE 7

Five hundred g of an aluminum nitrate aqueous solution (Al(NO$_3$)$_3$·9H$_2$O (Special Grade Chemical), manufactured by Wako Pure Chemical Industries, Ltd., dissolved in water to make up a concentration of 1.0 mol/liter), and 11.5 g of a cerium oxide sol ("NEEDRAL W-15," manufactured by Taki Chemical Co., Ltd.; CeO$_2$ concentration: 15% by weight) are mixed. To the mixture, water is added to make up a volume of 1 liter, yielding a starting material liquid mixture. Specifically, the concentrations of Al$_2$O$_3$ and CeO$_2$ in the starting material liquid mixture are, respectively, 0.25 mol/liter and 0.01 mol/liter, and the amount of the daughter-and-matrix particle mixture contained in the above starting material liquid mixture is 2.72% by weight.

In order to improve the dispersability of the fine particles in the above starting material liquid mixture and to get a uniforms blend of these fine particles, after the starting material liquid mixture is stirred for a given period of time, the mixture is subject to an ultrasonic dispersion treatment for about 30 minutes in the same manner as in Example 1. Thereafter, the temperature of a reaction pipe is set at 850° C., and the aluminum oxide ultrafine particles used as matrix particles are produced by evaporation of water and the pyrolysis of aluminum nitrate in the reaction pipe using the device mentioned in Example 1, to give composite fine particles.

The obtained particles are white, showing slightly smooth skin texture. The particle shapes are observed in the same manner as in Example 1. As a result, it is found that the particles are spherical particles having an average particle diameter of about 1 μm. Also, it is found that CeO$_2$ ultrafine particles (average particle diameter: about 0.01 μm) are dispersed in and supported by aggregates comprising Al$_2$O$_3$ ultrafine particles (average particle diameter: about 0.01 μm). In other words, the composite fine particles are CeO$_2$/Al$_2$O$_3$ composite fine particles; matrix particles are the aggregates of Al$_2$O$_3$ particles having a band gap energy of about 8.3 eV and a refractive index of about 1.73; and daughter particles are CeO$_2$ particles having a band gap energy of about 3 eV and a refractive index of about 2. Further, the crystallinity of the Al$_2$O$_3$ in the composite fine particles thus produced is evaluated by X-ray diffraction method. As a result, it is found to be a γ-type.

The amount of the daughter particles in the above composite fine particles is about 3.6% by volume, and the specific surface area of the composite fine particles as determined by the BET method is about 115 m$^2$/g. Here, the amount of the daughter particles is calculated from the compositional ratio of particles in the starting material liquid mixture, wherein particle densities of Al$_2$O$_3$ and CeO$_2$ are 3.99 g/cm$^3$ and 7.13 g/cm$^3$, respectively, and these values are used for the calculation.

Figure 7:
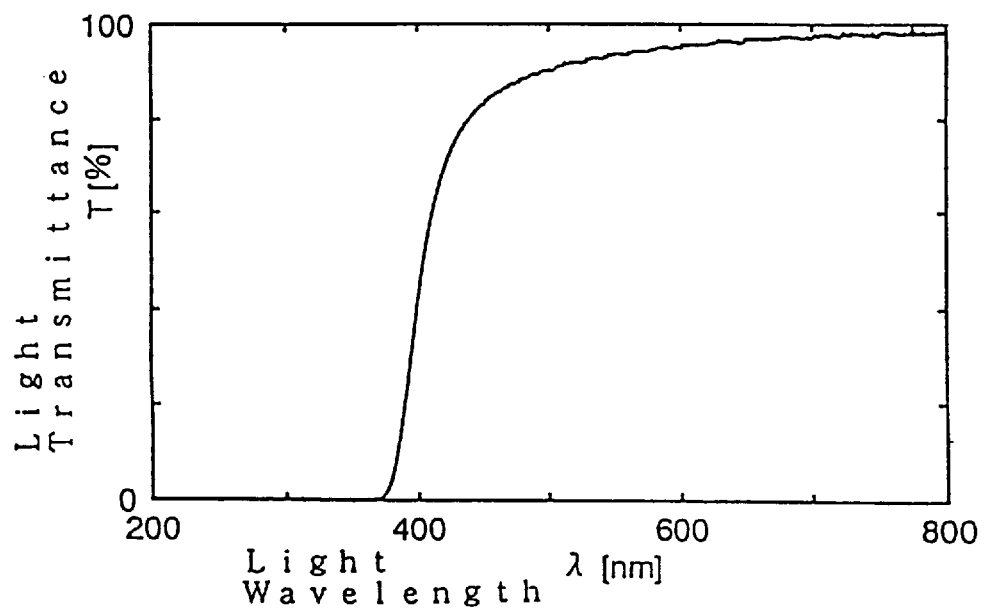
FIG. 7 is a graph showing the relationship between a light wavelength and a light transmittance of the ultraviolet shielding composite fine particles obtained in Example 7, as measured by an ultraviolet-visible light spectrophotometer.

Since the refractive index of the composite fine particles is about 1.74, as calculated from the volume ratio of the matrix particles to the daughter particles, 120 mg of the composite fine particles having the above refractive index is suspended in diiodomethane (refractive index: 1.74) used as a dispersion medium for the composite fine particles to prepare 2 g of diiodomethane suspension in which 6% by weight of the composite fine particles is suspended. The light transmittance of the obtained suspension is evaluated in the wavelength of from 200 to 800 nm in the same manner as in Example 1. The results are shown in FIG. 7.

In the figure, the light transmittance of the composite fine particles is substantially equal to 0% in the ultraviolet region A, the ultraviolet region B, and the ultraviolet region C, the wavelengths of which are not longer than 370 nm. At the same time, the composite fine particles show that the light transmittance at 400 nm is 41%, and the light transmittance at 800 nm is 98%. Accordingly, although the composite fine particles thus produced have a slightly yellowish coloring, they have a high transparency in the visible light region and a high shielding ability in the ultraviolet region.

EXAMPLE 8

51.2 g of a silica sol ("ST-C," manufactured by Nissan Chemical Industries, Ltd.; $SiO_2$ concentration: 20.5% by weight), 44.5 g of a magnesium fluoride sol ("MFS-10," manufactured by Nissan Chemical Industries, Ltd.; $MgF_2$ concentration: 10.5% by weight) are mixed. To the mixture, a zinc nitrate aqueous solution $(Zn(NO_3)_2 \cdot 6H_2O$ (Special-Grade-Chemical), manufactured by Wako Pure Chemical Industries, Ltd., dissolved in water to make up a concentration of 0.01 mol/liter) is added to make up a volume of 1 liter, yielding a starting material liquid mixture. Specifically, the concentrations of $SiO_2$, $MgF_2$, and $Zn(NO_3)_2$ in the starting material liquid mixture are, respectively, 0.175 mol/liter, 0.075 mol/liter and 0.01 mol/liter, and the amount of the daughter-and-matrix particle mixture contained in the above starting material liquid mixture is 1.52% by weight.

In order to improve the dispersability of the fine particles in the above starting material liquid mixture and to get a uniform blend of these fine particles, after the starting material liquid mixture is stirred for a given period of time, the mixture is subject to an ultrasonic dispersion treatment for about 30 minutes in the same manner as in Example 1. Thereafter, the temperature of a reaction pipe is set at 700° C., and the zinc oxide ultrafine particles which are daughter particles are produced by evaporation of water and the pyrolysis of zinc nitrate in the reaction pipe using the device mentioned in Example 1, to give composite fine particles. The formed composite fine particles dispersed in a nitrogen carrier gas are collected by a diffusion charging-type electrostatic collector in the same manner as in Example 1.

The obtained particles are white, showing a slightly smooth skin texture. The particles are observed in the same manner as in Example 1. As a result, it is found that the particles are spherical particles having an average particle diameter of about 1 $\mu$m. Also, it is found that the ZnO ultrafine particles (average particle diameter: about 0.01 $\mu$m) are dispersed in and supported by aggregates comprising a mixture of the $SiO_2$ ultrafine particles (average particle diameter: about 0.01 $\mu$m) and the $MgF_2$ ultrafine particles (average particle diameter: about 0.02 $\mu$m). In other words, the composite fine particles are $ZnO/(SiO_2+MgF_2)$ composite fine particles; matrix particles are the aggregates comprising $SiO_2$ particles and $MgF_2$ particles; and daughter particles are ZnO particles. Further, the crystallinity of ZnO in the composite fine particles thus produced is evaluated by X-ray diffraction method. As a result, it is found to be a wurtzite-type.

The amount of the daughter particles in the above composite fine particles is about 2.3% by volume, and the specific surface area of the composite fine particles as determined by the BET method is about 145 $m^2/g$. Here, the amount of the daughter particles is calculated from the compositional ratio of particles in the starting material liquid mixture, wherein particle densities of $SiO_2$, $MgF_2$, and ZnO are 2.27 $g/cm^3$, 3.15 $g/cm^3$, and 5.78 $g/cm^3$, respectively, and these values are used for the calculation.

Figure 8:
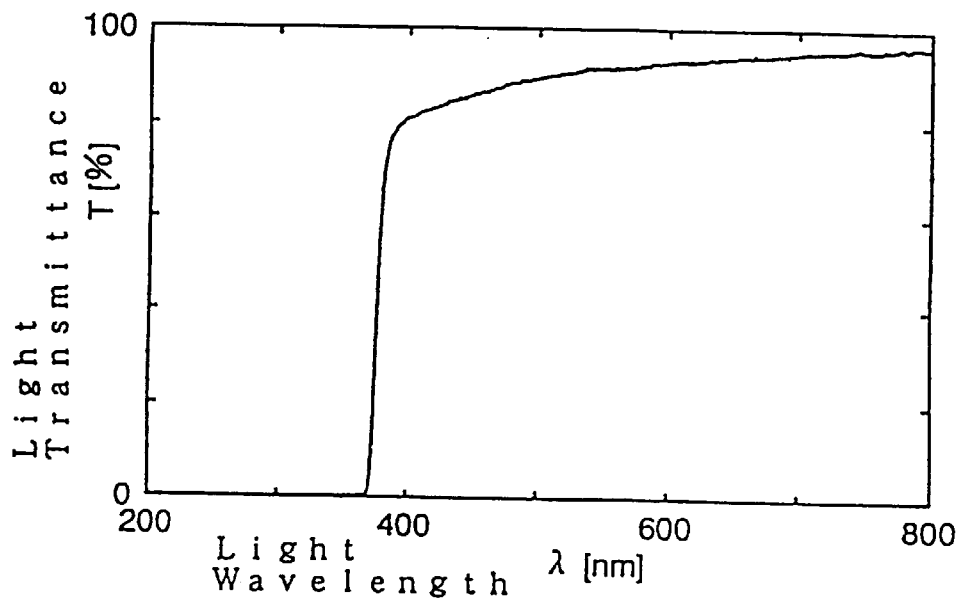
FIG. 8 is a graph showing the relationship between a light wavelength and a light transmittance of the ultraviolet shielding composite fine particles obtained in Example 8, as measured by an ultraviolet-visible light spectrophotometer.

Since the refractive index of the composite fine particles is about 1.45, as calculated from the volume ratio of the matrix particles to the daughter particles, 20 mg of the composite fine particles is suspended in a malic distearyl solution ("COSMOL 222," manufactured by The Nisshin Oil Mills, Ltd.; refractive index: 1.46) used as a dispersion medium for the composite fine particles to prepare 2 g of a suspension in which 1% by weight of the composite fine particles are suspended in malic distearyl. The light transmittance of the obtained suspension is evaluated in the same manner as in Example 1. The results are shown in FIG. 8.

In the figure, the light transmittance of the composite fine particles is substantially equal to 0% in the ultraviolet region A, the ultraviolet region B, and the ultraviolet region C, the wavelengths of which are not longer than 320 nm. At the same time, the composite fine particles show remarkably high light transmittance values in the entire visible light region at a wavelength of from 400 to 800 nm, as is seen from the results that the light transmittance at 400 nm is 81%, and the light transmittance at 800 nm is 96%. Accordingly, the composite fine particles thus produced have a high transparency in the visible light region and a high shielding ability in the ultraviolet region.

EXAMPLE 9

148 g of a magnesium fluoride sol ("MFS-10," manufactured by Nissan Chemical Industries, Ltd.; $MgF_2$ concentration: 10.5% by weight), and 0.814 g of zinc oxide ultrafine particles ("FINEX 75," manufactured by Sakai Chemical Industry Co., Ltd.) are mixed. To the mixture, water is added to make up a volume of 1 liter, yielding a starting material liquid mixture. Specifically, the concentrations of $MgF_2$ and ZnO in the starting material liquid mixture are, respectively, 0.25 mol/liter and 0.01 mol/liter, and the amount of the daughter-and-matrix particle mixture contained in the above starting material liquid mixture is 1.64% by weight.

The starting material liquid mixture is subject to a dispersion treatment in the same manner as in Example 5 using beads mill. After removal of the glass beads, drying is then carried out in the same manner as in Example 1 except that air is used as a carrier gas, and the set temperature of the drying tube is 500° C., to produce composite fine particles comprising matrix particles (aggregates of $MgF_2$ particles) and daughter particles (ZnO particles).

The obtained particles are white, showing a slightly smooth skin texture. The particles are observed in the same manner as in Example 1. As a result, it is found that the particles are spherical particles having an average particle diameter of about 1 $\mu$m. Also, it is found that ZnO ultrafine particles (average particle diameter: about 0.01 $\mu$m) are dispersed in and supported by aggregates of $MgF_2$ ultrafine particles (average particle diameter: about 0.02 $\mu$m). In other words, the composite fine particles are $ZnO/MgF_2$ composite fine particles; matrix particles are the aggregates of $MgF_2$ particles having a band gap energy of about 6 eV and a refractive index of about 1.38; and daughter particles are ZnO particles having a band gap energy of about 3.2 eV and a refractive index of about 1.99.

The amount of the daughter particles in the above composite fine particles is about 2.8% by volume, and the specific surface area of the composite fine particles as determined by the BET method is about 135 $m^2/g$. Here, the amount of the daughter particles is calculated from the compositional ratio of particles in the starting material liquid mixture, wherein particle densities of $MgF_2$ and ZnO are 3.15 $g/cm^3$ and 5.78 $g/cm^3$, respectively, and these values are used for the calculation.

Figure 9:
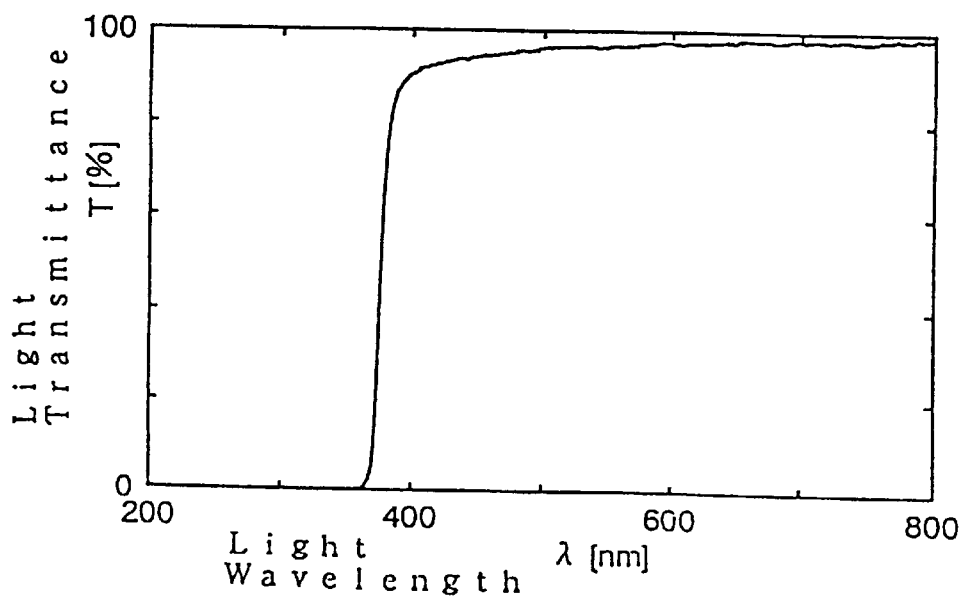
FIG. 9 is a graph showing the relationship between a light wavelength and a light transmittance of the ultraviolet shielding composite fine particles obtained in Example 9, as measured by an ultraviolet-visible light spectrophotometer.

Since the refractive index of the composite fine particles is about 1.40, as calculated from the volume ratio of the matrix particles to the daughter particles, 120 mg of the composite fine particles having the above refractive index is suspended in a 50% by weight glycerol aqueous solution (refractive index: 1.3996) used as a dispersion medium for the composite fine particles, to prepare 2 g of glycerol suspension in which 6% by weight of the composite fine particles is suspended. The light transmittance of the obtained suspension is evaluated in the same manner as in Example 1. The results are shown in FIG. 9.

In the figure, the light transmittance of the composite fine particles is substantially equal to 0% in the ultraviolet region A, the ultraviolet region B, and the ultraviolet region C, the wavelengths of which are not longer than 360 nm. At the same time, the composite fine particles show remarkably high light transmittance values in the entire visible light region at a wavelength of from 400 to 800 nm, as is seen from the results that the light transmittance at 400 nm is 90%, and the light transmittance at 800 nm is 98%. Accordingly, the composite fine particles thus produced have a high transparency in the visible light region and a high shielding ability in the ultraviolet region.

Incidentally, when the refractive index of the composite fine particles is measured by immersion method, the obtained value is 1.3996, showing substantially no difference from the refractive index calculated from the volume ratio given above.

EXAMPLE 10
(Lotion)

| Ingredients | Amount (weight %) |
| --- | --- |
| Ethanol | 30.0 |
| Glycerol | 5.0 |
| Polyethylene glycol 1500 | 4.0 |
| Polyoxyethylene(20) oleyl ether | 1.0 |
| Polyoxyethylene(30) hydrogenated castor oil | 0.5 |
| Composite Fine Particles (Produced in Example 1) | 10.0 |
| Urocanic acid | 2.0 |
| Perfume | 0.2 |
| Distilled Water | to 100 |

The lotion having the above composition is applied to human skin. It is found that the applied skin is free from unnatural whitening, and the cosmetics have an excellent ultraviolet shielding effect.

EXAMPLE 11
(Emulsion)

| Ingredients | Amount (weight %) |
| --- | --- |
| Cetanol | 1.0 |
| Squalane | 5.0 |
| Olive Oil | 8.0 |
| Octyl methoxycinnamate | 4.0 |
| Polyoxyethylene(10) hydrogenated castor oil | 1.0 |
| Sorbitan monostearate | 1.0 |
| Composite Fine Particles (Produced in Example 2) | 10.0 |
| Butyl p-hydroxybenzoate | 0.1 |
| Methyl p-hydroxybenzoate | 0.1 |
| Ethanol | 3.0 |
| Glycerol | 2.0 |
| 1,3-Butylene glycol | 2.0 |
| Perfume | 0.1 |
| Distilled Water | to 100 |

The emulsion having the above composition is applied to human skin. It is found that the applied skin is free from unnatural whitening, and the cosmetics have an excellent ultraviolet shielding effect.

EXAMPLE 12
(Cream)

| Ingredients | Amount (weight %) |
| --- | --- |
| Stearic Acid | 2.0 |
| Cetanol | 1.0 |
| Cholesterol | 1.0 |
| Squalane | 10.0 |
| Olive Oil | 5.0 |
| Octyl methoxycinnamate | 4.0 |
| Cetyl phosphate | 0.5 |
| Sorbitan monostearate | 2.0 |
| Polyoxyethylene(40) hydrogenated castor oil | 0.5 |
| Composite Fine Particles (Produced in Example 3) | 10.0 |
| Titanium Oxide Fine Particles | 2.0 |
| Butyl p-hydroxybenzoate | 0.1 |
| Methyl p-hydroxybenzoate | 0.1 |
| Glycerol | 10.0 |
| L-Arginine | 0.3 |
| Perfume | 0.1 |
| Distilled Water | to 100 |

The cream having the above composition is applied to human skin. It is found that the applied skin is free from unnatural whitening, and the cosmetics have an excellent ultraviolet shielding effect.

EXAMPLE 13
(Aerosol Cosmetics)

| Ingredients | Amount (weight %) |
| --- | --- |
| Triclosan | 0.01 |
| Aluminum hydroxychloride | 1.5 |
| Talc | 1.0 |
| Composite Fine Particles (Produced in Example 1) | 5.0 |
| Isopropyl myristate | 2.0 |
| Perfume | 0.2 |
| Propellant | to 100 |

The aerosol cosmetics having the above composition are applied to human skin. It is found that the cosmetics have an excellent ultraviolet shielding effect.

EXAMPLE 14

Comparative Examples 1 and 2

Each of cosmetics having the following composition shown in Table 1 is prepared.

TABLE 1

|  | Example 14 | Comparative Example 1 | Comparative Example 2 |
| --- | --- | --- | --- |
| Silicone-Treated Composite Fine Particles (Produced in Example 1) | 20 | — | — |
| Silicone-Treated Titanium Dioxide (Average particle diameter: 0.05–0.10 μm) | — | 10 | — |
| Silicone-Treated Titanium Dioxide Fine Particles (Average particle diameter: 0.01–0.05 μm) | — | — | 10 |
| Dimethylpolysiloxane | 5 | 5 | 5 |
| Dimethylcyclopolysiloxane | 20 | 20 | 20 |

TABLE 1-continued

|  | Example 14 | Comparative Example 1 | Comparative Example 2 |
|---|---|---|---|
| Dimethylsiloxane-methylpolyoxy-ethylene-siloxane copolymer | 3 | 3 | 3 |
| Glycerol | 5 | 5 | 5 |
| Perfume | q.s. | q.s. | q.s. |
| Distilled water | to 100 | to 100 | to 100 |
| Transparency after Applying Cosmetics[1)] | ◯ | X | ◯ |
| Ultraviolet Shielding Effects[2)] | ◯ | ◯ | X |

Notes
[1)]Change in color after applying cosmetics is determined by a color difference meter. The following evaluation is made:
◯: Having color difference($\Delta E$) of not more than 5.
X: Having color difference($\Delta E$) exceeding 5.
[2)]Ultraviolet shielding effects are evaluated by applying cosmetics onto backside of body and exposing to sunlight at seashore at the height of summer. The following evaluation is made:
◯: Erythema not detected even after 2 hours.
X: Erythema detected within 2 hours.

EXAMPLE 15

(Powdery Foundation)

| Ingredients | Amount (weight %) |
|---|---|
| (1) Fluorine Compound-Treated (*1) Composite Fine Particles (Produced in Example 3) | 10.0 |
| (2) Fluorine Compound-Treated (*1) Mica | 31.0 |
| (3) Fluorine Compound-Treated (*1) Talc | 20.0 |
| (4) Fluorine Compound-Treated (*1) Titanium Oxide | 8.0 |
| (5) Fluorine Compound-Treated (*1) Iron Oxide (Red, Yellow, Black) | 3.0 |
| (6) Fluorine Compound-Treated (*1) Zinc Oxide Fine Particles | 2.0 |
| (7) Fluorine Compound-Treated (*1) Titanium Oxide Fine Particles (Average Particle Diameter: 35 nm) | 1.0 |
| (8) Fluorine Compound-Treated (*1) Nylon Powder | 10.0 |
| (9) Dimethylpolysiloxane (10 cSt) | 4.0 |
| (10) Perfluoropolyether ("FOMBLIN HC-04," manufactured by AUSIMONT CO.) | 8.0 |
| (11) Hydrogenated Oil (Synchrowax) | 1.0 |
| (12) Octyl methoxycinnamate | 1.0 |
| (13) Antiseptics, Perfume | 1.0 |

Notes (*1): Treatment is carried out by coating with 5% by weight of perfluoroalkyl ethyl phosphate.

Ingredients (1) to (8) are blended in a Henshel mixer. Ingredients (9) to (13) subjected to blending and heating at 80° C. in advance are added to the mixture comprising the ingredients (1) to (8). The resulting mixture is pulverized using a pulverizer. A given amount of the pulverized product is taken out on a metallic pan, and pressed by a pressing machine, to give a powdery foundation.

The resulting powdery foundation has remarkably advantageous effects in shielding ultraviolet light and has good spreadability, and natural feeling after application.

EXAMPLE 16

(Cake-Foundation)

| Ingredients | Amount (weight %) |
|---|---|
| (1) Silicone-Treated (*2) Composite Fine Particles (Produced in Example 2) | 20.0 |
| (2) Silicone-Treated (*2) Mica | to 100 |
| (3) Silicone-Treated (*2) Talc | 20.0 |
| (4) Silicone-Treated (*2) Titanium Oxide | 9.0 |
| (5) Silicone-Treated (*2) Iron Oxide (Red, Yellow, Black) | 4.0 |
| (6) Silicone-Treated (*2) Zinc Oxide Fine Particles Coated with 30% by weight of Nylon Powder | 8.0 |
| (7) Dimethylpolysiloxane (10,000 cSt) | 0.2 |
| (8) Dimethylpolysiloxane (6 cSt) | 8.0 |
| (9) Hydrogenated Oil (Synchrowax) | 1.0 |
| (10) Octyl methoxycinnamate | 2.0 |
| (11) Antiseptics, Perfume | 1.0 |

Notes (*2): Treatment is carried out by coating with 5% by weight of methylhydrogenpolysiloxane.

Ingredients (1) to (6) are blended in a Henshel mixer. Ingredients (7) to (11) subjected to blending and heating at 80° C. in advance are added to the mixture comprising the ingredients (1) to (6). The resulting mixture is pulverized using a pulverizer. A given amount of the pulverized product is taken out on a metallic pan, and pressed by a pressing machine, to give a cake-foundation.

The resulting cake-foundation has remarkably advantageous effects in shielding ultraviolet light and have good spreadability, and natural feeling after application.

EXAMPLE 17

(Powdery Eye Shadow)

| Ingredients | Amount (weight %) |
|---|---|
| (1) Lecithin-Treated (*3) Composite Fine Particles (Produced in Example 1) | 5.0 |
| (2) Lecithin-Treated (*3) Mica | to 100 |
| (3) Lecithin-Treated (*3) Titanated Mica | 6.0 |
| (4) Lecithin-Treated (*4) Ultramarine | 8.0 |
| (5) Lecithin-Treated (*4) Prussian blue | 10.0 |
| (6) Lecithin-Treated (*4) Iron Oxide (Red, Yellow, Black) | 2.0 |
| (7) Spherical Silicone Resin Powder ("TOSPAL 145," manufactured by Toshiba Silicone Co.) | 10.0 |
| (8) Dimethylpolysiloxane (6 cSt) | 6.0 |
| (9) Diisostearyl malate | 3.0 |
| (10) Hydrogenated Oil (Synchrowax) | 0.5 |
| (11) Vaseline | 1.0 |
| (12) Antiseptics, Perfume | 1.0 |

Notes
(*3): Treatment is carried out by coating with 5% by weight of soybean lecithin.
(*4): Treatment is carried out by coating with 2% by weight of methylhydrogenpolysiloxane.

Ingredients (1) to (7) are blended in a Henshel mixer. Ingredients (8) to (12) subjected to blending and heating at 80° C. in advance are added to the mixture comprising the ingredients (1) to (7). The resulting mixture is pulverized using a pulverizer. A given amount of the pulverized product is taken out on a metallic pan, and pressed by a pressing machine, to give a powdery eye shadow.

The resulting powdery eye shadow has remarkably advantageous effects in shielding ultraviolet light and has good spreadability, and provides good coloring to the skin.

EXAMPLE 18
(Emulsion Type's Foundation)

| Ingredients | Amount (weight %) |
|---|---|
| (1) Silicone-Treated (*5) Composite Fine Particles (Produced in Example 4) | 4.0 |
| (2) Silicone-Treated (*5) Titanium Oxide | 3.0 |
| (3) Silicone-Treated (*5) Iron Oxide (Red, Yellow, Black) | 1.5 |
| (4) Silicone-Treated (*5) Zinc Oxide Fine Particles | 3.0 |
| (5) Dimethylcyclopolysiloxane | 20.0 |
| (6) Dimethylpolysiloxane (6 cSt) | 10.0 |
| (7) Octyl methoxycinnamate | 2.0 |
| (8) Dimethylsiloxane-methylpolyoxyethylene-siloxane copolymer | 1.0 |
| (9) Glycerol | 2.0 |
| (10) Ethanol | 10.0 |
| (11) Distilled water | to 100 |

Notes (*5): Treatment is carried out by coating with 2% by weight of methylhydrogenpolysiloxane.

Ingredients (1) to (4) are blended in a Henshel mixer. Ingredients (5) to (8) are separately blended, and the mixture comprising the ingredients (1) to (4) blended in advance is added to a mixture comprising the ingredients (5) to (8), and the obtained mixture is dispersed with a stirrer. A mixture comprising ingredients (9) to (11) is gradually added over a period of 30 minutes to the above dispersed mixture while stirring. The obtained mixture containing all ingredients listed above is then emulsified by stirring with a homomixer for 10 minutes. The obtained emulsion is defoamed, and then filled into a bottle to give a emulsion type's foundation.

The resulting emulsion type's foundation has remarkably advantageous effects in shielding ultraviolet light and has good spreadability, and natural feeling after application.

EXAMPLE 19
(Lipstick)

| Ingredients | Amount (weight %) |
|---|---|
| (1) Silicone-Treated (*6) Composite Fine Particles (Produced in Example 1) | 1.0 |
| (2) Silicone-Treated (*6) Pigment Red 57-1 | 1.0 |
| (3) Silicone-Treated (*6) Pigment Red 57 | 2.0 |
| (4) Silicone-Treated (*6) Acid Yellow 23 Aluminum Lake | 1.0 |
| (5) Silicone-Treated (*6) Titanium Oxide | 1.0 |
| (6) Paraffin wax | 5.0 |
| (7) Candelilla wax | 10.0 |
| (8) Carnauba wax | 9.0 |
| (9) Isopropyl isopalmitate | 20.0 |
| (10) Isononyl isononanate | 15.0 |
| (11) Isostearyl malate | 30.0 |
| (12) Dimethylpolysiloxane (1000 cSt) | 5.0 |

Notes (*6): Treatment is carried out by coating with 2% by weight of methylhydrogenpolysiloxane.

Ingredients (1) to (12) are heated to 80° C. and blended to give a homogeneous mixture, and the obtained mixture is cooled to a temperature of 30° C. The cooled mixture is sufficiently blended with a triple roller, and then reheated to 80° C. The obtained mixture is casted into a mold and then solidified by cooling to give a lipstick.

The resulting lipstick has remarkably advantageous effects in shielding ultraviolet light and has good spreadability, and provides good coloring to the lip.

INDUSTRIAL APPLICABILITY

When the composite fine particles of the present invention are dispersed in a solid or liquid medium, the composite fine particles show high light transmittance in the visible light region, and exhibit a high shielding ability in the ultraviolet region. Accordingly, the composite fine particles are useful as ultraviolet shielding agents in cosmetics. The cosmetics containing the composite fine particles have good smoothness, excellent extensibility on skin, substantially no unevenness, excellent transparency, no unnatural skin whitening, and high ultraviolet shielding effects. Further, since the composite fine particles have excellent transparency, the coloring of the cosmetics is not affected.

We claim:

1. Ultraviolet shielding composite fine particles having transparency in a visible light region, comprising:

(a) matrix particles comprising an aggregate of primary particles having an average particle diameter of from 0.001 to 0.3 $\mu$m, said aggregate being formed while retaining the shapes of the primary particles; and (b) daughter particles having an average particle diameter of from 0.001 to 0.1 $\mu$m, said daughter particles being dispersed in and supported by said matrix particles, wherein said daughter particles have a smaller band gap energy than that of particles constituting said matrix particles, and possess capability of absorbing ultraviolet light.

2. The ultraviolet shielding composite fine particles according to claim 1, wherein said particles constituting the matrix particles have a band gap energy of from 3 to 9 eV.

3. The ultraviolet shielding composite fine particles according to claim 1 or 2, wherein a difference of the band gap energies between the daughter particles and the particles constituting the matrix particles is not less than 0.2 eV.

4. The ultraviolet shielding composite fine particles according to claim 1 or 2, wherein said daughter particles are dispersed in and supported by said matrix particles in a proportion of from 0.1 to 50% by volume.

5. The ultraviolet shielding composite fine particles according to claim 1 or 2, wherein an average refractive index of the ultraviolet shielding composite fine particles is from 1.3 to 1.8.

6. The ultraviolet shielding composite fine particles according to claim 1 or 2, wherein an average particle diameter of the ultraviolet shielding composite fine particles is from 0.1 to 500 $\mu$m.

7. The ultraviolet shielding composite fine particles according to claim 1 or 2, wherein a specific surface area of the ultraviolet shielding composite fine particles is less than 250 m$^2$/g.

8. The ultraviolet shielding composite fine particles according to claim 1 or 2, wherein said particles constituting the matrix particles are selected from the group consisting of metal oxides, flourine-containing compounds, and mixtures thereof.

9. The ultraviolet shielding composite fine particles according to claim 8, wherein said metal oxide is selected from the group consisting of $SiO_2$, $Al_2O_3$, and a mixture thereof.

10. The ultraviolet shielding composite fine particles according to claim 8, wherein said fluorine-containing compound is selected from the group consisting of $MgF_2$, polytetrafluoroethylene, and a mixture thereof.

11. The ultraviolet shielding composite fine particles according to claim 8, wherein said particles constituting the matrix particles are produced using as starting materials a metal oxide and/or a fluorine-containing compound being in a solid state at room temperature, and further using perfluoropolyether.

12. The ultraviolet shielding composite fine particles according to claim 1 or 2, wherein said daughter particles are selected from the group consisting of $TiO_2$, ZnO, $CeO_2$, $BaTiO_3$, $CaTiO_3$, $SrTiO_3$, SiC, and mixture thereof.

13. The ultraviolet shielding composite fine particles according to claim 1 or 2, wherein a light transmittance at 800 nm is not less than 90%, a light transmittance at 400 nm is not less than 40%, and a light transmittance at one or more of wavelengths of 350 nm, 320 nm, and 300 nm is not more than 5%, the light transmittance being measured by an ultraviolet-visible light spectrophotometer using an optical cell having an optical path length of 1 mm, wherein a sample of the ultraviolet shielding composite fine particles is suspended in a medium having substantially the same refractive index as the refractive index of the sample, wherein a difference within ±0.1 in the refractive index is defined as substantially the same.

14. The ultraviolet shielding composite fine particles according to claim 1 or 2, wherein said composite fine particles are obtainable by a method comprising the steps of:
   (a) preparing a liquid mixture containing a mixture comprising:
      (i) starting materials for matrix particles selected from the group consisting of a sol containing particles constituting the matrix particles, primary particles of said matrix particles having an average particle diameter of from 0.001 to 0.3 μm, a solution capable of producing said particles constituting the matrix particles by a pyrolysis reaction, and mixtures thereof; and
      (ii) starting materials for daughter particles selected from the group consisting of a sol containing daughter particles having an average particle diameter of from 0.001 to 0.1 μm, a powder of said daughter particles, a solution capable of producing said daughter particles by a pyrolysis reaction, and mixtures thereof;
   (b) forming droplets from said liquid mixture; and
   (c) drying the formed droplets and/or pyrolyzing starting materials for pyrolysis therein.

15. A method for producing ultraviolet shielding composite fine particles having transparency in a visible light region comprising:
   matrix particles comprising an aggregate of primary particles having an average particle diameter of from 0.001 to 0.3 μm, said aggregate being formed while retaining the shapes of the primary particles; and
   daughter particles having an average particle diameter of from 0.001 to 0.1 μm, said daughter particles being dispersed in and supported by said matrix particles, wherein said daughter particles have a smaller band gap energy than that of particles constituting said matrix particles, and possess capability of absorbing ultraviolet light,
said method comprising the steps of:
   (a) preparing a liquid mixture containing less than 5% by weight of a mixture comprising starting materials for the matrix particles and starting materials for the daughter particles, prepared by mixing:
      (i) starting materials for matrix particles selected from the group consisting of a sol containing particles constituting the matrix particles, primary particles of said matrix particles having an average particle diameter of from 0.001 to 0.3 μm, a solution capable of producing said particles constituting the matrix particles by a pyrolysis reaction, and mixtures thereof; and
      (ii) starting materials for daughter particles selected from the group consisting of a sol containing daughter particles having an average particle diameter of from 0.001 to 0.1 μm, a powder of said daughter particles, a solution capable of producing said daughter particles by a pyrolysis reaction, and mixtures thereof, so as to have a daughter particle concentration of from 0.1 to 50% by volume in a whole solid volume;
   (b) forming droplets from said liquid mixture; and
   (c) drying the formed droplets and/or pyrolyzing starting materials for pyrolysis therein, the drying and/or pyrolyzing steps being carried out in an atmosphere of from 100° to 1000° C.

16. The method according to claim 15, wherein said steps comprises:
   (a) preparing a liquid mixture containing less than 5% by weight of a particle mixture prepared by mixing a sol containing particles constituting the matrix particles, primary particles of said matrix particles having an average particle diameter of from 0.001 to 0.3 μm and a sol containing daughter particles having an average particle diameter of from 0.001 to 0.1 μm, so as to have a daughter particle concentration of from 0.1 to 50% by volume in a whole solid volume;
   (b) forming droplets having an average droplet diameter of from 0.1 to 2000 μm from said liquid mixture; and
   (c) drying the formed droplets in an atmosphere of from 100° to 1000° C.

17. The method according to claim 15, wherein said steps comprise:
   (a) preparing a liquid mixture by disintegrating or pulverizing a powder of daughter particles having an average particle diameter of from 0.001 to 0.1 μm in a sol containing particles constituting the matrix particles, primary particles of said matrix particles having an average particle diameter of from 0.001 to 0.3 μm, so as to have a daughter particle concentration of from 0.1 to 50% by volume in a whole solid volume;
   (b) forming droplets having an average droplet diameter of from 0.1 to 2000 μm from said liquid mixture; and
   (c) drying the formed droplets in an atmosphere of from 100° to 1000° C.

18. Cosmetics comprising ultraviolet shielding composite fine particles of claim 1.

19. The cosmetics according to claim 18, wherein said ultraviolet shielding composite fine particles are subject to a hydrophobic treatment.

20. The cosmetics according to claim 18 or 19, wherein the cosmetics are used for ultraviolet blocking.

21. The cosmetics according to claim 18 or 19, further containing an ultraviolet protecting agent.

22. The cosmetics according to claim 18 or 19, wherein the amount of said ultraviolet shielding composite fine particles is from 0.1 to 60% by weight.

* * * * *